US012708650B2

(12) United States Patent
Zhang et al.

(10) Patent No.: US 12,708,650 B2
(45) Date of Patent: Aug. 18, 2026

(54) RECOMBINANT BACTERIA AND USES THEREOF

(71) Applicant: National University of Singapore, Singapore (SG)

(72) Inventors: Yongliang Zhang, Singapore (SG); Chin Wen Png, Singapore (SG)

(73) Assignee: National University of Singapore, Singapore (SG)

( * ) Notice: Subject to any disclaimer, the term of this patent is extended or adjusted under 35 U.S.C. 154(b) by 886 days.

(21) Appl. No.: 17/310,833

(22) PCT Filed: Feb. 28, 2020

(86) PCT No.: PCT/SG2020/050095
§ 371 (c)(1),
(2) Date: Aug. 26, 2021

(87) PCT Pub. No.: WO2020/176042
PCT Pub. Date: Sep. 3, 2020

(65) Prior Publication Data

US 2022/0133817 A1 May 5, 2022

(30) Foreign Application Priority Data

Feb. 28, 2019 (SG) ............................ 10201901828T

(51) Int. Cl.

| | |
|---|---|
| ***A61K 35/744*** | (2015.01) |
| ***A61K 38/16*** | (2006.01) |
| ***A61K 39/395*** | (2006.01) |
| ***A61P 35/00*** | (2006.01) |
| ***C12N 9/16*** | (2006.01) |

(52) U.S. Cl.
CPC .......... *A61K 35/744* (2013.01); *A61K 38/164* (2013.01); *A61K 39/3955* (2013.01); *A61P 35/00* (2018.01); *C12N 9/16* (2013.01); *C12Y 301/03016* (2013.01); *C12Y 301/03048* (2013.01)

(58) Field of Classification Search
None
See application file for complete search history.

(56) References Cited

U.S. PATENT DOCUMENTS

| | | | | |
|---|---|---|---|---|
| 6,133,023 | A | 10/2000 | Madsen et al. | |
| 2003/0138449 | A1* | 7/2003 | Langermann ........ | C07K 14/245 424/190.1 |
| 2004/0086859 | A1 | 5/2004 | Klaus | |
| 2007/0037145 | A1 | 2/2007 | Morris et al. | |
| 2010/0179213 | A1 | 7/2010 | Patrawala et al. | |
| 2013/0209405 | A1 | 8/2013 | Curtiss, III et al. | |
| 2015/0071957 | A1 | 3/2015 | Kelly et al. | |
| 2015/0265692 | A1 | 9/2015 | Entenza et al. | |

FOREIGN PATENT DOCUMENTS

| | | | |
|---|---|---|---|
| CN | 107073094 | A | 8/2017 |
| JP | 2000-236873 | A | 9/2000 |
| JP | 2002-097144 | A | 4/2022 |
| WO | 2017/167213 | A1 | 10/2017 |
| WO | 2020176042 | A1 | 9/2020 |

OTHER PUBLICATIONS

Dennis et al. "Current status of IL-10 and regulatory T-cells in cancer". Curr Opin Oncol. 2013, 15(6): 637-645.*
Collins et al. "Combining vaccine and immune checkpoint inhibitors to prime, expand and facilitate effective tumor immunotherapy". Expert Rev Vaccines, 2018, 17(8): 697-705.*
Terzic et al. "Inflammation and Colon Cancer". Gastroenterology. 2010, vol. 138, No. 2, pp. 2101-2114.*
Yang et al. "Construction of recombinant adenovirus encoding PTEN cDNA", Accession No. 2005:1330192 CAPLUS; Source: Dier Junyi Daxue Xuebao (2004), 25(5), 556-558.*
Kim et al. "Two-promoter vector is highly efficient for overproduction of protein complexes". Protein Science. 2004, 13:1698-1703.*
Almeida, Juliana F. et al. "Expression of fibronectin binding protein A (FnBPA) from *Staphylococcus aureus* at the cell surface of Lactococcus lactis improves its immunomodulatory properties when used as protein delivery vector." Vaccine 34.10 (2016): 1312-1318.
Del Carmen, S. et al. "A novel interleukin-10 DNA mucosal delivery system attenuates intestinal inflammation in a mouse model." European Journal of Inflammation 11.3 (2013): 641-654.
International Application No. PCT/SG2020/050095, International Search Report and Written Opinion mailed Jun. 15, 2020.

(Continued)

*Primary Examiner* — Vera Afremova
(74) *Attorney, Agent, or Firm* — Kilpatrick Townsend Stockton LLP

(57) ABSTRACT

The present disclosure provides a recombinant, probiotic lactic acid bacterium, wherein the bacterium comprises a non-replicating plasmid vector comprising (a) a tumor suppressor gene or anti-inflammatory gene operably linked to a first promoter that directs expression of the tumor suppressor gene or anti-inflammatory gene in a mammalian cell, and (b) an adhesin gene operably linked to a second promoter that directs expression of the adhesin gene in the bacterium. The present disclosure also provides uses of the recombinant bacterium, and methods of constructing the recombinant bacterium. The present disclosure also provides a method of treating cancer in a subject, wherein the method comprises administering a pharmaceutically effective amount of a recombinant, probiotic lactic acid bacterium, wherein the bacterium comprises a non-replicating plasmid vector comprising an adhesin gene operably linked to a promoter that directs expression of the adhesin gene in the bacterium.

10 Claims, 11 Drawing Sheets

Specification includes a Sequence Listing.

(56) References Cited

OTHER PUBLICATIONS

Pereira, Vanessa Bastos et al. "Development of a new DNA vaccine based on mycobacterial ESAT-6 antigen delivered by recombinant invasive Lactococcus lactis FnBPA+." Applied microbiology and biotechnology 99.4 (2015): 1817-1826.
Png, C. W. et al. "DUSP10 regulates intestinal epithelial cell growth and colorectal tumorigenesis." Oncogene 35.2 (2016): 206-217.
Pontes, Daniela et al. "Production of fibronectin binding protein A at the surface of Lactococcus lactis increases plasmid transfer in vitro and in vivo." (2012): e44892.
Souza, Bianca Mendes et al. "Lactococcus lactis carrying the pValac eukaryotic expression vector coding for IL-4 reduces chemically-induced intestinal inflammation by increasing the levels of IL-10-producing regulatory cells." Microbial cell factories 15.1 (2016): 1-18.
Veloso, Tiago Rafael et al. "Vaccination against *Staphylococcus aureus* experimental endocarditis using recombinant Lactococcus lactis expressing ClfA or FnbpA." Vaccine 33.30 (2015): 3512-3517.
Zhang, Yongliang et al. "Regulation of innate and adaptive immune responses by MAP kinase phosphatase 5." Nature 430.7001 (2004): 793-797.
Ciaćma et al., "Secretion of Tumoricidal Human Tumor Necrosis Factor-Related Apoptosis-Inducing Ligand (TRAIL) by Recombinant *Lactococcus lactis*: Optimization of In Vitro Synthesis Conditions", Microbial Cell Factories, vol. 17, No. 177, Nov. 16, 2018, 16 pages.
European Application No. EP20762387.7, "Extended European Search Report", Nov. 2, 2022, 11 pages.
Mathipa & Thantsha, "Probiotic Engineering: Towards Development of Robust Probiotic Strains with Enhanced Functional Properties and for Targeted Control of Enteric Pathogens", Gut Pathogens, vol. 9, No. 28, May 8, 2017, 17 pages.
Baban, Chwanrow K. et al., "Bacteria as vectors for gene therapy of cancer," Bioengineered Bugs, 2010, 1:6 pp. 385-394.
Japanese Application No. 2021-550152, "Office Action," mailed Feb. 29, 2024, 10 pages (5 pages original, 5 pages translation).
Nonn, Larisa et al., "Chemopreventive anti-inflammatory activities of curcumin and other phytochemicals mediated by MAP kinase phosphatase-5 in prostate cells," Carcinogenesis, 2007, vol. 28, No. 6, pp. 1188-1196.
Almeida et al., "Correlation between Fibronectin Binding Protein A Expression Level at the Surface of Recombinant Lactococcus Lactis and Plasmid Transfer in Vitro and In Vivo", BMC Microbiology, vol. 14, Dec. 2014, pp. 1-8.
CN Application No. 202080026498.2 , "Office Action", May 11, 2024, 12 pages.
CN Application No. 202080026498.2 , "Office Action", Dec. 24, 2024, 15 pages.
CN Application No. 202080026498.2 , "Office Action", Oct. 15, 2024, 15 pages.
CN Application No. 202080026498.2 , "Office Action", Nov. 28, 2023, 18 pages.
JP Application No. 2021-550152 , "Notice of Decision to Grant", Feb. 10, 2025, 6 pages.
JP Application No. 2021-550152 , "Office Action", Sep. 26, 2024, 10 pages.
Kim et al., "Cancer Preventive Effect of Recombinant TRAIL by Ablation of Oncogenic Inflammation in Colitis-associated Cancer Rather Than Anticancer Effect", Oncotarget, vol. 9, No. 2, Dec. 7, 2017, pp. 1705-1716.
Menezes et al., "Role of MDA-7/IL-24 a Multifunction Protein in Human Diseases", Advances in Cancer Research, vol. 138, Jan. 2018, pp. 143-182.
MY Application No. PI2021004951 , "Substantive Examination Adverse Report", Jun. 12, 2024, 5 pages.
OFT , "IL-10: Master Switch from Tumor-Promoting Inflammation to Antitumor Immunity", Cancer Immunology Research, vol. 2, No. 3, Mar. 2014, pp. 194-199.
SG Application No. 11202109383X , "Written Opinion", Feb. 20, 2023, 6 pages.
Examination Report issued in AU 2020229628 dated Sep. 25, 2025, 5 pages.

* cited by examiner

A

B

A

B

C

A

1 = Untreated
2 = Vect
3 = Lactis-DUSP10
4 = anti-PDL-1
5 = anti-PDL-1 + Vect
6 = anti-PDL-1 + Lactis-DUSP10

Note: Image shows the most severe case within each group

B

*P < 0.05 (compared to untreated, 1-way ANOVA)

RECOMBINANT BACTERIA AND USES THEREOF

CROSS-REFERENCE TO RELATED APPLICATIONS

This application claims the benefit of priority of Singapore patent application No. 10201901828T, filed 28 Feb. 2019, the contents of it being hereby incorporated by reference in its entirety for all purposes.

FIELD OF THE INVENTION

The present invention relates to microbiology and molecular biology, in particular the development of recombinant bacterium, and the use of recombinant bacterium in treating cancer.

BACKGROUND OF THE INVENTION

Colorectal cancer, or cancer of the colon and rectum, is the third most common neoplasm worldwide and the most commonly diagnosed cancer in Singapore.

Surgery is the main form of treatment for colorectal cancer. However, surgery removes bulk tumor, leaving behind microscopic residual disease which ultimately results in recrudescence.

For Stages II and III, radiation therapy may be added to help kill the cancer and shrink the tumor. Radiation may also be used in Stage IV to improve symptoms and prolong life. However, the use of radiation therapy as a single modality in the definitive treatment of colorectal cancer has met with little success despite efforts to increase the total dose to the tumor and reduce the amount of irradiated normal tissue. Radiation therapy is rarely helpful in patients with colorectal cancer that is unsuitable for resection, as the usual reason for nonresectability is the lack of anatomic localization of the cancer. Radiation therapy is sometimes used to relieve localized obstruction, particularly in the region of the cardia, and for patients with chronically bleeding cancers that cannot be resected. The median survival for patients treated with radiation is around 12 months, and long-term survivors are few.

Many chemotherapeutic drugs have been tried in the past as single agents for the palliation of colorectal cancer, but the results were generally disappointing. Nevertheless, the role of chemotherapy in the management of colorectal cancer is continually evolving. Active chemotherapeutic agents include 5-fluorouracil, IMC-C225 (cetuximab), leucovorin, irinotecan, oxaliplatin, Camptosar (Pharmacia & Upjohn), and Celebrex. Oftentimes, chemotherapy with radiation in adjunct to surgery is used. In general, chemotherapy can achieve long-term survival rates of up to 15% to 20%, even in patients with recurrent or metastatic disease. Unfortunately, the high initial response rate to first line chemotherapy does not appear to translate into a survival benefit. Moreover, there are many undesirable side effects associated with chemotherapy such as temporary hair loss, mouth sores, anemia (decreased numbers of red blood cells that may cause fatigue, dizziness, and shortness of breath), leukopenia (decreased numbers of white blood cells that may lower resistance to infection), thrombocytopenia (decreased numbers of platelets that may lead to easy bleeding or bruising), and gastrointestinal symptoms like nausea, vomiting, and diarrhea.

While surgery, chemotherapeutic agents, and radiation are useful in the treatment of colorectal cancer, there is a continued need to find better treatment modalities and approaches to manage the disease that are more effective and less toxic, especially when clinical oncologists are giving increased attention to the quality of life of cancer patients.

SUMMARY OF THE INVENTION

In one aspect, there is provided a recombinant, probiotic lactic acid bacterium, wherein the bacterium comprises a non-replicating plasmid vector comprising (a) a tumor suppressor gene or anti-inflammatory gene operably linked to a first promoter that directs expression of the tumor suppressor gene or anti-inflammatory gene in a mammalian cell, and (b) an adhesin gene operably linked to a second promoter that directs expression of the adhesin gene in the bacterium.

In another aspect, there is provided a method of treating cancer or reducing inflammation in a subject, wherein the method comprises administering a pharmaceutically effective amount of the recombinant, probiotic lactic acid bacterium of the present invention into the gastrointestinal tract of the subject, and wherein the cancer or inflammation is a cancer or inflammation of the gastrointestinal tract.

In another aspect, there is provided a method of treating cancer in a subject, wherein the method comprises administering a pharmaceutically effective amount of a recombinant, probiotic lactic acid bacterium, wherein the bacterium comprises a non-replicating plasmid vector comprising an adhesin gene operably linked to a promoter that directs expression of the adhesin gene in the bacterium.

BRIEF DESCRIPTION OF THE DRAWINGS

The invention will be better understood with reference to the detailed description when considered in conjunction with the non-limiting examples and the accompanying drawings, in which:

FIG. 3A are representative images showing Caco2 and DLD1 xenograft tumours developed in immunocompromised mice after 18 days post-administration. FIG. 3B shows bar charts summarizing the size and weight of the respective xenografts. Mean±standard deviations are shown. * and ** represent P<0.05 and P<0.01 respectively (Mann-Whitney test). The results show that DUSP10 overexpression reduced tumour growth in vivo.

FIG. 4A shows representative images (left panel) and H&E micrographs (right panel) showing metastatic lesions (red arrows) developed in liver of immunocompromised mice after intra-splenic injection of either DUSP10 overexpression or control HCT116 cells. FIG. 4B shows bar charts summarizing quantitative measurement of liver weight, total tumour load per liver and largest tumour size. Mean±standard deviations are shown.  and * represent P<0.01 and P<0.001 respectively (Mann-Whitney test). The results show that overexpression of DUSP10 reduced metastatic colonisation of HCT116 cells to the liver in an intra-splenic injection mouse model.

FIG. 6A is a bar chart showing the mRNA level, and FIG. 6B is a western blot imaging showing the protein level, of DUSP10 in uninfected and various *L. lactis* infected Caco2 cells (MOI=1500). FIG. 6C is a bar chart showing the percentage of Caco2 proliferation after 3 days of daily infection with various *L. lactis* bacteria. 1=uninfected cells, 2=cells infected with *L. lactis* bacteria with control vector, 3=cells infected with *L. lactis* bacteria with Fnb only, 4=cells infected with *L. lactis* bacteria with DUSP10. Mean±standard deviations are shown.  and * represent P<0.01 and P<0.001 respectively (1-way ANOVA). The results demonstrate that Caco2 cells infected with *L. lactis*-Fnb-DUSP10 showed increased DUSP10 expression and resulted in suppression of cell proliferation.

FIG. 7A shows representative images of colon tumours found in AOM/DSS induced CRC mice with or without various *L. lactis* treatment through oral gavage. Top and bottom dot plots in FIG. 7B and FIG. 7C show the number of tumours per colon and average tumour size from each group of mice respectively. Mean percentage reduction in tumour load and size compared to untreated control is shown under each dot plot. Mean±standard deviations and 1-way ANOVA (*) P values are shown. The results show that treatment with *L. lactis*-Fnb-DUSP10 for 7 had successfully suppressed intestinal tumour development in the AOM/DSS induced CRC mouse model.

FIG. 8A shows representative image of caecum containing tumour (black arrows). FIG. 8B is a bar chart showing weight of caecum in untreated and treated mice. Mean±standard deviations are shown. *P<0.05 (Student's T test). The results show that the size of the transplanted Ls174T xenografts was smaller in mice treated with *L. lactis*-Fnb-DUSP10.

FIG. 9A shows representative H&E (Haemotoxylin and Eosin) micrographs for colonic inflammation, FIG. 9B is a dot plot showing histological scores for colonic inflammation. FIG. 9C shows weight change in mice during 2% DSS and *L. lactis* treatment. FIG. 9D shows changes in mRNA expression level of genes involved in inflammation. 1=Unt; 2=Vect; 3=Fnb; and 4=DUSP10. "Unt", "Vect", "Fnb" and "DUSP10" denote; untreated, *Lactis*-vector, *Lactis*-Fnb and *Lactis*-Fnb-DUSP10 treated groups, "PC" and "DC" refer to proximal and distal colon respectively. *,  and * denote P<0.05, <0.01 and <0.001 respectively (One-way ANOVA, Kruskal-Wallis test). Mean±standard deviations were shown in each graph. All statistical comparison were made to untreated control group.

FIG. 10A shows representative images of colon tumours found in AOM/DSS induced CRC mice with or without various *L. lactis* and/or anti-PDL-1 treatment. The dot plot in FIG. 10B shows the number of tumours per colon from each group of mice. Mean percentage reduction in tumour load compared to untreated control is shown under each dot plot. Mean±standard deviations and 1-way ANOVA (*) P values are shown. "Unt", "Vect", "*Lactis*-DUSP10", "anti-PDL-1", "anti-PDL-1+Vect" and "anti-PDL-1+*Lactis*-DUSP10" denote: untreated, *Lactis*-vector, *Lactis*-Fnb-DUSP10, anti-PDL-1, anti-PDL-1+*Lactis*-vector, and anti-PDL-1+*Lactis*-Fnb-DUSP10 treated groups. The results show that *L. lactis*-Fnb-DUSP10 and *L. lactis*-Fn-DUSP10+anti-PDL-1 treated groups had successfully suppressed intestinal tumour development in the AOM/DSS induced CRC mouse model.

DETAILED DESCRIPTION OF THE PRESENT INVENTION

Figure 1:
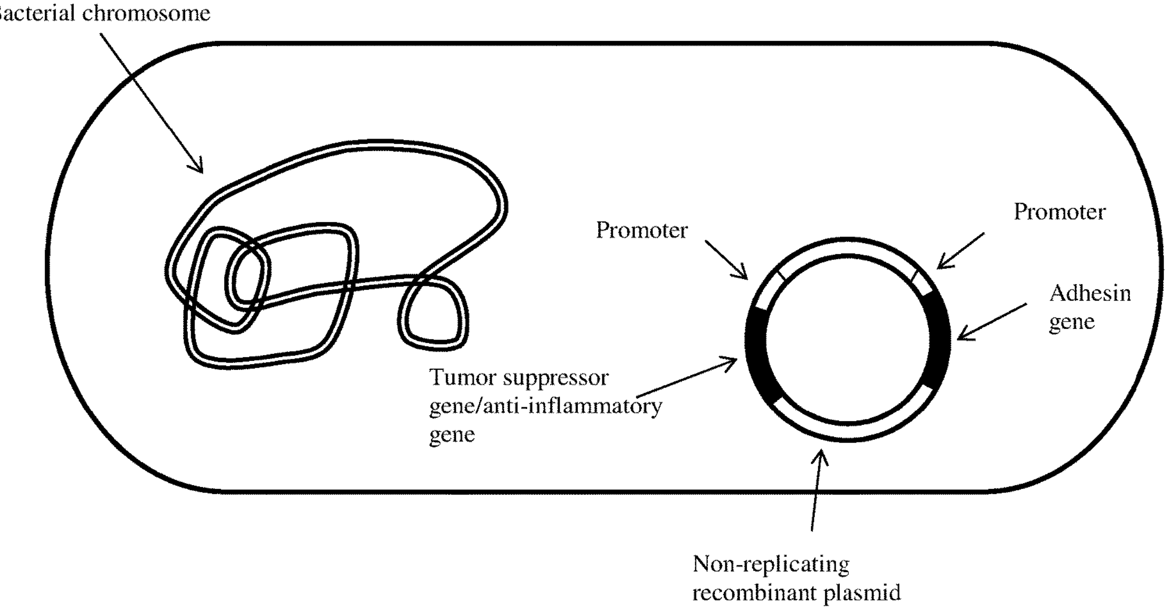
FIG. 1 provides illustration of examples of the recombinant bacteria of the present invention, where a single non-replicating recombinant plasmid comprises both the adhesin gene and the tumor suppressor/anti-inflammatory gene.

It has been found by the inventors that delivering non-replicating plasmid vector to the host cells allows better control of the expression of the genetic materials contained in the plasmid vector, thus resulting in improved control of the treatment regime which comprises the expression of the genetic materials in the host cells. Thus, in one aspect, there is provided a recombinant, probiotic lactic acid bacterium, wherein the bacterium comprises a non-replicating plasmid vector comprising (a) a tumor suppressor gene or anti-inflammatory gene operably linked to a first promoter that directs expression of the tumor suppressor gene or anti-inflammatory gene in a mammalian cell, and (b) an adhesin gene operably linked to a second promoter that directs expression of the adhesin gene in the bacterium.

The term "recombinant bacterium" as used herein refers to a bacterium containing recombinant genetic materials such as recombinant DNA molecule(s). Recombinant DNA molecules are usually formed by laboratory methods of genetic recombination (such as molecular cloning) to bring together genetic materials from multiple sources, creating sequences that would not otherwise be found in the genome. It is well understood that the DNA of most bacteria is contained in a single circular molecule, called the bacterial chromosome. In addition to the bacterial chromosome, bacteria often contain plasmids, which are small circular DNA molecules that are physically separated from the bacterial chromosome, which can replicate independently. In some examples, the recombinant bacterium contains recombinant DNA molecule(s) in the plasmids.

The term "probiotic" as used herein refers to non-pathogenic and non-toxigenic microorganisms, in particular bacteria, that perform beneficial functions for the host organism. The gastrointestinal tract of mammalian species harbors a complex microbial ecosystem containing a large number and variety of bacteria. The resident bacterial population in the gastrointestinal tract has a major impact on gastrointestinal function and thereby on the health and wellbeing of the host organism. Among these, some bacteria are opportunistic or considered to be detrimental and cause adverse conditions such as diarrhea, infections, gastroenteritis and endotoxaemia, while some bacteria species are considered as "probiotic", in that they perform beneficial functions for the host organism.

The term "lactic acid bacteria" or its grammatical variants as used herein refers to an order of gram-positive, low-GC, acid-tolerant, generally nonsporulating, nonrespiring, either rod-shaped (bacilli) or spherical (cocci) bacteria that share common metabolic and physiological characteristics. These bacteria, usually found in decomposing plants and milk products, produce lactic acid as the major metabolic end product of carbohydrate fermentation. Examples of lactic acid bacteria include *Lactococcus, Lactobacillus, Leuconostoc, Pediococcus, Streptococcus, Aerococcus, Carnobacterium, Enterococcus, Oenococcus, Sporolactobacillus, Tetragenococcus, Vagococcus*, and *Weissella*.

Lactococcus is a genus of lactic acid bacteria. They are gram-positive, catalase-negative, non-motile cocci that are found singly, in pairs, or in chains. Lactococcus are known as homofermenters, which means that they produce a single product, lactic acid in this case, as the major or only product of glucose fermentation. Twelve species of *Lactococcus* are currently recognized: *L. chungangensis, L. formosensis, L. fujiensis, Lactococcus hircilactis, L. garvieae* (*L. garvieae* subsp. garvieae, *L. garvieae* subsp. bovis), *L. lactis* (*L. lactis* subsp. cremoris, *L. lactis* subsp. hordniae, *L. lactis* subsp. lactis, *L. lactis* subsp. tructae), *L. laudensis, L. nasutitermitis, L. piscium, L. plantarum, L. raffinolactis* and *L. taiwanensis*.

In one specific example, the recombinant, probiotic lactic acid bacterium is of the *L. lactis* species. *L. lactis* is a Gram-positive bacterium used extensively in the production of buttermilk and cheese. *L. lactis* cells are cocci that group in pairs and short chains, and, depending on growth conditions, appear ovoid with a typical length of 0.5-1.5 μm. *L. lactis* does not produce spores (nonsporulating) and are not motile (nonmotile). *L. lactis* produce lactic acid from sugars. The capability to produce lactic acid is one of the reasons why *L. lactis* is one of the most important microorganisms in the dairy industry. Based on its history in food fermentation, *L. lactis* has generally recognized as safe (GRAS) status with few case reports of being an opportunistic pathogen. GRAS is a United States Food and Drug Administration (FDA) designation that a chemical or substance added to food is considered safe by experts, and so is exempted from the usual Federal Food, Drug, and Cosmetic Act (FFDCA) food additive tolerance requirements. In some examples, the recombinant, probiotic lactic acid bacterium, or the recombinant lactic acid producing bacterium, or the bacterium of the Lactococcus genus as disclosed herein is classified as a GRAS bacterium.

The term "express" or its grammatical variants as used herein refers to the transcription from DNA to an RNA nucleic acid molecule at least complementary in part to a region of one of the two nucleic acid strands of the gene, followed by the translation from said RNA nucleic acid molecule to give a protein or polypeptide or a portion thereof.

The term "adhesin" as used herein refers to cell-surface components or appendages of bacteria that facilitate adhesion or adherence to other cells or to surfaces, usually the host cells they are infecting or living in. Adherence is an essential step in bacterial pathogenesis or infection, required for colonizing a new host. In some bacteria, adhesins also function as invasins, which are a class of proteins associated with the penetration of bacteria into host cells. Invasins play a role in promoting entry during the initial stage of bacterial infection. Examples of the adhesin expressed in the recombinant bacteria of the present invention include fibronectin-binding protein and internalin.

Fibronectin is a multidomain glycoprotein found ubiquitously in human body fluids and extracellular matrices of a variety of human tissues and organs. After secretion, fibronectin molecules bind to transmembrane integrins, which facilitate dimerization and cytoskeletal coupling. The integrin-bound fibronectin is capable of binding to ECM components such as collagen and laminin. Human fibronectin plays a major role in the regulation of cell migration, tissue repair, and adhesion. Fibronectin is also a common target for bacterial adhesins in the gastrointestinal tract. Fibronectin-binding proteins (FnBPs) have been identified in a wide variety of host-associated bacteria. For example, fibronectin-binding protein A (FnBPA) and FnBPB function as adhesins and/or invasins for *Staphylococcus aureus* infection.

Internalins are surface proteins found on *Listeria monocytogenes*. They exist in two known forms, InlA and InlB. They are used by the bacteria to invade mammalian cells via cadherins transmembrane proteins and Met receptors respectively. In cultured cells, InlA is necessary to facilitate Listeria entry into human epithelial cells, while InlB is necessary for Listeria internalisation in several other cell types, including hepatocytes, fibroblasts, and epithelioid cells. The term "non-replicating plasmid vector" as used herein refers to a plasmid vector that cannot replicate in the mammalian host cells after being delivered to the mammalian host cells. The inventors of the present invention found that use of non-replicating plasmid vectors allows improved control of a treatment regime that involves the delivery of the plasmid vectors into the mammalian host cells. For example, any adverse reaction due to the delivery of the plasmid vectors can be controlled or terminated readily upon discontinuation of the treatment. This is because mammalian host cells infected with the recombinant bacteria of the present invention will not be able to pass on the plasmid vector to their daughter cells, hence any adverse effect will be restricted to the primary cells that have been infected, which will stop naturally at the end of the life-span of the infected cells. The use of non-replicating plasmid vectors also allows fine tuning of the dosage (i.e. the expression of the genes contained in the plasmid vectors) over time to achieve optimal clinical efficacy, which may vary among different patients. The non-replicating plasmid vectors are generally constructed with the bacterial origin of replication (ori), with no other factors such as EBV or SV40 ori and their corresponding antigen components that can facilitating replication in mammalian cells. As such, the resulting construct(s) are able to replicate in the recombinant bacterium as disclosed herein, but are not able to replicate in the mammalian host cells.

Expressing adhesin(s) in bacteria allows the bacteria to infect its host cells in the gastrointestinal tract of a host organism, when the bacteria have been administered to the gastrointestinal tract of the host organism. Since probiotic lactic acid bacteria are generally recognized as safe bacteria, the inventors of the present invention postulate that probiotic lactic acid bacteria that express adhesin(s) can be used to deliver genetic materials to the cells of the host organism, in particular the cells in the gastrointestinal tract of the host organism, after the cells in the gastrointestinal tract of the host organism are infected by the bacteria.

It is preferred that the genetic material being delivered to the cells of the host organism is beneficial to the host organism. For example, when the cells of the host organism being infected by the bacteria are tumor cells, and the genetic material being delivered to the cells encodes for tumor suppressor proteins, then the bacteria can be used for treating tumor in the host organism. In preferred embodiments, the genetic material being delivered to the cells only suppress the growth of the tumor cells but not the growth of the healthy non-tumor cells.

The term "tumor suppressor gene" or its grammatical variants as used herein refers to a type of gene that makes a protein called a tumor suppressor protein that helps control cell growth. Mutations in tumor suppressor genes may lead to cancer.

The term "anti-inflammatory gene" or its grammatical variants as used herein refers to a type of gene that makes a protein that helps to prevent inflammation or reduce the symptoms of inflammation.

In some examples, the tumor suppressor gene or anti-inflammatory gene has tumor-suppressing or anti-inflammatory effects on cells of the gastrointestinal tract. Examples of tumor suppressor genes include TP53, APC, CD95, PTEN, TRAIL, MDA7, and PMAIP1. Examples of anti-inflammatory genes include IL10, IL11, IL13, IL1-ra, and TGFb. In some examples, anti-inflammatory genes being delivered to the host cells can induce the expression of other anti-inflammatory genes, or suppress the expression of pro-inflammatory genes. Examples of pro-inflammatory genes include IL1b, IL6,IL18 and TNFα.

In one specific example, the tumor suppressor gene or anti-inflammatory gene being delivered to the host organism is a DUSP10 gene. DUSP10 is a protein coding gene that encodes for DUSP10 (Dual Specificity Phosphatase 10), also known as MAP kinase phosphatase 5 (MKP5). An exemplary sequence of DUSP10 gene is set out in SEQ ID NO: 1, and an exemplary sequence of DUSP10 protein is set out in SEQ ID NO: 10.

Dual specificity protein phosphatases inactivate their target kinases by dephosphorylating both the phosphoserine/threonine and phosphotyrosine residues. They negatively regulate members of the MAP kinase superfamily, which is associated with cellular proliferation and differentiation. Different members of this family of dual specificity phosphatases show distinct substrate specificities for MAP kinases, different tissue distribution and subcellular localization, and different modes of expression induction by extracellular stimuli.

DUSP10 targets the mitogen-activated protein kinases (MAPK, including ERK 1/2), which is downstream of the highly represented EGFR-KRAS-BRAF-MEK-ERK1/2 pathway in colorectal cancer. Multiple gene mutations within this pathway that result in increased ERK1/2 activity are characteristic of colorectal cancer. Since DUSP10 targets the downstream effector ERK1/2, its therapeutic effect is less likely to be affected by the mutations in the upstream effectors of the EGFR-KRAS-BRAF-MEK-ERK1/2 pathway. In addition, inflammatory status/activity of the infected cells could also be controlled, since DUSP10 is a negative regulator of the MAKPs pathway, which is a major intermediate factor for the development of immune responses.

The genetic material being delivered to the cells of the host organism would result in the expression of the gene(s) of interest in the genetic material within the cells of the gastrointestinal tract of the host organism. This means the gene(s) of interest would preferably not be expressed or not be significantly expressed in the bacteria of the present invention in the extracellular/luminal compartment of the gastrointestinal tract of the host organism. Rather, the bacteria are merely operating as a vehicle that delivers the genetic material to the cells of the host organism. The advantage is that the gene product(s), such as the tumor suppressor and/or the anti-inflammatory protein, will be expressed directly in the cells in which the tumor suppressing and/or anti-inflammatory effect is to be exerted. To order to achieve this, gene(s) of interest in the genetic material being delivered should be regulated by a promoter that drives the expression of the gene(s) of interest in the eukaryotic cells, and preferably a promoter that is does not drive the expression of the gene(s) of interest in prokaryotic cells such as bacterial cells. As used herein, the term "eukaryote" or "eukaryotic" refers to organisms or cells or tissues derived therefrom belonging to the phylogenetic domain Eukarya such as animals (e.g. mammals, insects, reptiles, and birds), ciliates, plants (e.g. monocots, dicots, and algae), fungi, yeasts, flagellates, microsporidia, and protists. The term "prokaryote", "prokaryotic cell" or "non-eukaryotic organism" refers to organisms including, but not limited to, organisms of the Archaea domain and the Bacteria domain.

In some preferred examples, the cells of the host organism, in particular mammalian organism, are only transiently transfected by the genetic materials being delivered by the recombinant bacterium. Thus, the first promoter that directs expression of the DUSP10 gene can be a promoter from mammalian viruses. Examples of such promoters include (i) the polyhedrin promoter from baculovirus (PH promoter), (ii) the enhancer and immediate early promoter from cytomegalovirus (CMV promoter), (iii) the early promoter from simian vacuolating virus 40 (SV40 promoter), (iv) the thymidine kinase promoter from HSV1 (TK promoter), and (v) the 5'LTR promoter from HIV (LTR promoter). Sequences of these exemplary promoters are set out in SEQ ID NOs: 2-6 in Table 1. Thus, in some examples, the first promoter that directs expression of the DUSP10 gene in a mammalian cell is a PH promoter, a CMV promoter, a SV40 promoter, a TK promoter or a LTR promoter.

TABLE 1

Exemplary sequences of viral promoters

| SEQ ID NO: | Promoter | Sequence |
|---|---|---|
| 2 | PH promoter | ATCATGGAGATAATTAAAATGATAACCATCTCGCAAATAAA<br>TAAGTATTTTACTGTTTTCGTAACAGTTTTGTAATAAAAAAA<br>CCTATAAATATTCCGGATTATTCATACCGTCCCACCATCGGG<br>CGCG |
| 3 | CMV promoter | TAGTAATCAATTACGGGGTCATTAGTTCATAGCCCATATAT<br>GGAGTTCCGCGTTACATAACTTACGGTAAATGGCCCGCCTG<br>GCTGACCGCCCAACGACCCCCGCCCATTGACGTCAATAATG<br>ACGTATGTTCCCATAGTAACGCCAATAGGGACTTTCCATTG<br>ACGTCAATGGGTGGAGTATTTACGGTAAACTGCCCACTTGG<br>CAGTACATCAAGTGTATCATATGCCAAGTACGCCCCCTATT<br>GACGTCAATGACGGTAAATGGCCCGCCTGGCATTATGCCCA<br>GTACATGACCTTATGGGACTTTCCTACTTGGCAGTACATCTA<br>CGTATTAGTCATCGCTATTACCATGGTGATGCGGTTTTGGCA<br>GTACATCAATGGGCGTGGATAGCGGTTTGACTCACGGGGAT<br>TTCCAAGTCTCCACCCCATTGACGTCAATGGGAGTTTGTTTT<br>GGCACCAAAATCAACGGGACTTTCCAAAATGTCGTAACAAC<br>TCCGCCCCATTGACGCAAATGGGCGGTAGGCGTGTACGGTG<br>GGAGGTCTATATAAGCAGAGCTGGTTTAGTGAACCGTCAG |

TABLE 1-continued

Exemplary sequences of viral promoters

| SEQ ID NO: | Promoter | Sequence |
|---|---|---|
| 4 | SV40 promoter | CTGTGGAATGTGTGTCAGTTAGGGTGTGGAAAGTCCCCAGG CTCCCCAGCAGGCAGAAGTATGCAAAGCATGCATCTCAATT AGTCAGCAACCAGGTGTGGAAAGTCCCCAGGCTCCCCAGCA GGCAGAAGTATGCAAAGCATGCATCTCAATTAGTCAGCAAC CATAGTCCCGCCCCTAACTCCGCCCATCCCGCCCCTAACTCC GCCCAGTTCCGCCCATTCTCCGCCCCATGGCTGACTAATTTT TTTTATTTATGCAGAGGCCGAGGCCGCCTCTGCCTCTGAGCT ATTCCAGAAGTAGTGAGGAGGCTTTTTTGGAGGCCTAGGCT TTTGCAAAAAGCTC |
| 5 | TK promoter | AAATGAGTCTTCGGACCTCGCGGGGGCCGCTTAAGCGGTGG TTAGGGTTTGTCTGACGCGGGGGGAGGGGGAAGGAACGAA ACACTCTCATTCGGAGGCGGCTCGGGGTTTGGTCTTGGTGG CCACGGGCACGCAGAAGAGCGCCGCGATCCTCTTAAGCACC CCCCCGCCCTCCGTGGAGGCGGGGGTTTGGTCGGCGGGTGG TAACTGGCGGGCCGCTGACTCGGGCGGGTCGCGCGCCCCAG AGTGTGACCTTTTCGGTCTGCTCGCAGACCCCCGGGCGGCG CCGCCGCGGCGGCGACGGGCTCGCTGGGTCCTAGGCTCCAT GGGGACCGTATACGTGGACAGGCTCTGGAGCATCCGCACG ACTGCGGTGATATTACCGGAGACCTTCTGCGGGACGAGCCG GGTCACGCGGCTGACGCGGAGCGTCCGTTGGGCGACAAAC ACCAGGACGGGGCACAGGTACACTATCTTGTCACCCGGAGG CGCGAGGGACTGCAGGAGCTTCAGGGAGTGGCGCAGCTGC TTCATCCCCGTGGCCCGTTGCTCGCGTTTGCTGGCGGTGTCC CCGGAAGAAATATATTTGCATGTCTTTAGTTCTATGATGAC ACAAACCCCGCCCAGCGTCTTGTCATTGGCGAATTCGAACA CGCAGATGCAGTCGGGGCGGCGCGGTCCCAGGTCCACTTCG CATATTAAGGTGACGCGTGTGGCCTCGAACACCGAGCGACC CTGCAGCGACCCGCTTAA |
| 6 | LTR promoter | TGGAAGGGCTAATTCACTCCCAACGAAGACAAGATATCCTT GATCTGTGGATCTACCACACACAAGGCTACTTCCCTGATTA GCAGAACTACACACCAGGGCCAGGGATCAGATATCCACTG ACCTTTGGATGGTGCTACAAGCTAGTACCAGTTGAGCCAGA GAAGTTAGAAGAAGCCAACAAAGGAGAGAACACCAGCTTG TTACACCCTGTGAGCCTGCATGGAATGGATGACCCGGAGAG AGAAGTGTTAGAGTGGAGGTTTGACAGCCGCCTAGCATTTC ATCACATGGCCCGAGAGCTGCATCCGGAGTACTTCAAGAAC TGCTGACATCGAGCTTGCTACAAGGGACTTTCCGCTGGGGA CTTTCCAGGGAGGCGTGGCCTGGGCGGGACTGGGGAGTGG CGAGCCCTCAGATCCTGCATATAAGCAGCTGCTTTTTGCCTG TACTGGGTCTCTCTGGTTAGACCAGATCTGAGCCTGGGAGC TCTCTGGCTAACTAGGGAACCCACTGCTTAAGCCTCAATAA AGCTTGCCTTGAGTGCTTCAAGTAGTGTGTGCCCGTCTGTTG TGTGACTCTGGTAACTAGAGATCCCTCAGACCCTTTTAGTCA GTGTGGAAAATCTCTAGC |

A plasmid vector comprising a tumor suppressor gene or anti-inflammatory gene is inserted into the probiotic lactic acid bacterium in order for the bacterium to deliver the gene to the cells of the host organism of the bacterium. In order for the tumor suppressor gene or anti-inflammatory gene to be expressed and hence exert its effect on the cells or the host organism, the tumor suppressor gene or anti-inflammatory gene is operably linked to the first promoter that directs expression of the gene in a host cell, in particular a mammalian cell.

The term "operably link" or its grammatically variants as used herein means that a gene of interest, a linker (if any), and a promoter are joined as part of the same nucleic acid molecule, suitably positioned and oriented for transcription of the gene of interest to be initiated from the promoter. In some examples, it means the tumor suppressor gene or anti-inflammatory gene, the first promoter, and optionally a linker, are joined as part of the plasmid vector, suitably positioned and oriented for transcription of the gene to be initiated from the first promoter.

The term "vector" as used herein refers to a DNA molecule used as a vehicle to artificially carry foreign genetic material into another cell, where it can be replicated and/or expressed. Different host cells have characteristic and specific mechanisms for the post-translational processing and modification of proteins. Expression vectors for use in mammalian cells ordinarily include an origin of replication, a promoter located in front of the gene to be expressed, along with any necessary ribosome binding sites, RNA splice sites, polyadenylation site, and transcriptional terminator sequences.

The term "plasmid" as used herein refers to a small DNA molecule within a cell that is physically separated from a chromosomal DNA and can replicate independently. They are most commonly found as small circular, double-stranded DNA molecules in bacteria. In nature, plasmids often carry genes that may benefit the survival of the organism, for example antibiotic resistance. While the chromosomes are big and contain all the essential genetic information for living under normal conditions, plasmids usually are very small and contain only additional genes that may be useful to the organism under certain situations or particular conditions.

Specific initiation signals may also be required for efficient translation of exogenous nucleic acid coding sequences. These signals include the ATG initiation codon and adjacent sequences. Exogenous translational control signals, including the ATG initiation codon, may additionally need to be provided in the vector. One of ordinary skill in the art would readily be capable of determining this need and providing the necessary signals. It is well known that the initiation codon must be in-frame (or in-phase) with the reading frame of the desired coding sequence to ensure translation of the entire insert. Exogenous translational control signals and initiation codons can be of a variety of origins, both natural and synthetic. The efficiency of expression may be enhanced by the inclusion of appropriate transcription enhancer elements or transcription terminators. In eukaryotic expression, an appropriate polyadenylation site (e.g., 5'-AATAAA-3') can also be incorporated into the transcriptional unit if not contained within the original cloned segment. Typically, the poly A addition site is placed about 30 to 2000 nucleotides downstream of the termination site of the protein at a position prior to transcription termination.

The adhesin in the recombinant bacterium can be expressed from a plasmid vector comprising an adhesin gene, or a gene encoding for an adhesion, wherein adhesin gene and a gene encoding for an adhesion can be used interchangeable in the present disclosure. Thus, in some examples, the recombinant bacterium as disclosed in comprises a plasmid vector comprising an adhesin gene operably linked to a second promoter that directs expression of the adhesin gene in the bacterium. In another example, the recombinant bacterium as disclosed in comprises a plasmid vector comprising an adhesin gene operably linked to a second promoter that directs expression of a gene encoding for an adhesin in the bacterium. Fibronectin-binding protein is an example of adhesins. Non-limiting examples of fibronectin-binding protein include fibronectin-binding protein A (FnBPA) (SEQ ID NO: 12) and fibronectin-binding protein B (FnBPB) (SEQ ID NO: 13), wherein FnBPA and FnBPB had similar functions in terms of their binding ability to fibronectin. An exemplary sequence of the fibronectin-binding protein A gene is set out in SEQ ID NO: 7, and an exemplary sequence of the fibronectin-binding protein B gene is set out in SEQ ID NO: 11. In some preferred examples, the second promoter does not direct expression of the adhesin gene in a host cell, in particular a mammalian host cell. For example, the second promoter can be a prokaryotic promoter. A prokaryotic promoter typically comprises two short sequences at −10 and −35 positions upstream from the transcription start site. The sequence at −10 is called the Pribnow box, or the −10 element, and usually consists of the six nucleotides TATAAT. The Pribnow box is essential to start transcription in prokaryotes. The other sequence at −35 is called the −35 element, and usually comprises the six nucleotides TTGACA. In one specific example, the prokaryotic promoter used to drive the expression of the adhesin gene is the erm promoter. An exemplary sequence of the erm promoter is set out in SEQ ID NO: 8. In some examples, inducible promoter is used. An example of an inducible promoter that can be used in Lactococcus is the nisin promoter. An exemplary sequence of the nisin promoter is set out in SEQ ID NO: 9.

The plasmid vector comprising the tumor suppressor gene or anti-inflammatory gene can be the same plasmid vector as the plasmid vector comprising the adhesin gene, provided that expressions of the tumor suppressor gene or anti-inflammatory gene and the adhesin gene are directed by different promoters, such that the tumor suppressor gene or anti-inflammatory gene will only be expressed in the host cells after the host cells have been infected by the bacterium, and that the adhesin gene will be expressed in the bacterium. It is preferred that the host cells are cells of a mammalian organism. Thus, in some examples, the recombinant bacterium comprises a plasmid vector comprising a tumor suppressor gene or anti-inflammatory gene operably linked to a first promoter that directs expression of the tumor suppressor gene or anti-inflammatory gene in a mammalian cell, and an adhesin gene operably linked to a second promoter that directs expression of the adhesin gene in the bacterium. In another example, the recombinant bacterium comprises a plasmid vector comprising a tumor suppressor gene or anti-inflammatory gene operably linked to a first promoter that directs expression of the tumor suppressor gene or anti-inflammatory gene in a mammalian cell, and an adhesin gene operably linked to a second promoter that directs expression of a gene encoding for an adhesin in the bacterium.

The plasmid vector comprising the tumor suppressor gene or anti-inflammatory gene can be a different plasmid vector as the plasmid vector comprising the adhesin gene or a gene encoding for an adhesin, provided that expressions of the tumor suppressor gene or anti-inflammatory gene and the adhesin gene are directed by different promoters, such that the tumor suppressor gene or anti-inflammatory gene will only be expressed in the host cells after the host cells have been infected by the bacterium, and that the adhesin gene or gene encoding for an adhesin will be expressed in the bacterium. It is preferred that the host cells are cells of a mammalian organism. Thus, in some examples, the recombinant bacterium comprises a first plasmid vector comprising a tumor suppressor gene or anti-inflammatory gene operably linked to a first promoter that directs expression of the tumor suppressor gene or anti-inflammatory gene in a mammalian cell, and a second plasmid vector comprising a adhesin gene operably linked to a second promoter that directs expression of the adhesin gene in the bacterium. In another example, the recombinant bacterium comprises a first plasmid vector comprising a tumor suppressor gene or anti-inflammatory gene operably linked to a first promoter that directs expression of the tumor suppressor gene or anti-inflammatory gene in a mammalian cell, and a second plasmid vector comprising a gene encoding for an adhesin operably linked to a second promoter that directs expression of the gene encoding for an adhesin in the bacterium It is to be noted that the terms "first" and "second" as used do not indicate or imply the relative positions or significance of the promoters and/or the plasmid vectors. When a plasmid vector comprises both the first promoter and the second promoter, it is understood that the first promoter and the second promoter are different, in order for the two promoters to direct the expression of the adhesin gene or the gene encoding for an adhesin, and the tumor suppressor gene or anti-inflammatory gene respectively. Similarly, when the recombinant bacterium comprises both the first plasmid vector and the second plasmid vector, it is understood that the first plasmid vector and the second plasmid vector are different, and they contain the expression cassettes for the adhesin gene or the gene encoding for an adhesin, and the tumor suppressor gene or anti-inflammatory gene respectively.

The recombinant bacterium of the present invention can be constructed using methods known in the art, which generally involve the construction of the plasmid vector(s), the transformation of the resultant plasmid vector(s) into the wild-type probiotic lactic acid bacteria, the identification and/or isolation of the bacteria that have been successfully transformed.

The construction of the plasmid vector(s) can be done by modifying a commercially available vector backbone that can be replicated in probiotic lactic acid bacteria, in particular lactococcal vector backbones. Examples of such vector backbone include, pTRKH3-ermGFP (Plasmid #27169 from addgene), pCD4, pHP003, pSRQ700, pSRQ800, pSRQ900, pK214, pAH90, pAH33, pAH82, pCIS3, pIL105, pWV01, pCI305, pCRL1127, pMN5, pBL1, pDR1-1B, pDR1-1, pS7b, pMRC01, pCRL291.1, pNZ4000, pBM02, pCL2.1, pWV02 (reviewed in FEMS Microbiology Review (2006) 30:243), pNZ8008, pNZ8148, pNZ8149, pNZ8150, pNZ9530 and derivatives of pSH71. The vector backbone will be digested using a restriction enzyme to linearize the vector backbone and to create sites for DNA ligation. Each of the gene(s) of interest, in this case the adhesin gene and/or the tumor suppressor gene or anti-inflammatory gene, is ligated to the linearized vector backbone to form the plasmid vector(s) to be transformed into the bacterial cells.

Transformation of the plasmid vector(s) into the bacterial cells can be carried out using methods known in the art. Such methods generally involve making the bacterial cells passively permeable to DNA by exposing them to conditions that do not normally occur in nature. Commonly used methods include electroporation method and heat-shock method. In an electroporation method, the bacterial cells are typically briefly shocked with an electric field of 10-20 kV/cm, which is thought to create holes in the cell membrane through which the plasmid vector(s) may enter. After the electric shock, the holes are rapidly closed by the cells' membrane-repair mechanisms. In a heat-shock method, the cells are incubated in a solution containing divalent cations under cold conditions, before being exposed to a heat pulse (heat shock). The cations partially disrupt the cell membrane, which allows the DNA to enter the host cell. It is suggested that exposing the cells to divalent cations in cold condition may also change or weaken the cell surface structure, making it more permeable to DNA. The heat-pulse is thought to create a thermal imbalance across the cell membrane, which forces the DNA to enter the cells through either cell pores or the damaged cell wall.

The vector backbones that are commercially available for use in molecular cloning typically contain one or more antibiotic resistance gene. After the transformation steps have been carried out, the resultant bacteria will be placed on an antibiotic-containing culture plate to select for the cells that have been successfully transformed. Since bacterial cells that have not been transformed successfully would not have acquired the antibiotic resistance gene, only those that have been successfully transformed would survive on the plate and form colonies. Each colony contains a cluster of identical plasmid-containing bacterial. Several colonies will usually be selected, and each of them will be checked to identify the colon(ies) containing the desired plasmid vector(s), by polymerase chain reaction (PCR) sequencing and/or restriction digest. A colony of bacteria identified to contain the desired plasmid vector(s) can then be grown in bulk.

The recombinant bacteria of the present invention can deliver exogenous tumor suppressor gene or anti-inflammatory gene to eukaryote cells in vivo or in vitro. The delivery requires contact and internalization of the recombinant bacteria by the target cells. Internalization can occur through one or more different mechanisms. The contacting between the recombinant bacteria and target cells can be induced to occur in vivo or in vitro. Typically, the contacting occurs in vivo.

Since increased level of expression of tumor suppressor gene or anti-inflammatory gene can suppress cancer cell proliferation and/or reduce inflammation, the recombinant bacterium of the present invention can be used for the treatment of cancer and/or inflammation. Thus, in one aspect, there is provided a method of treating cancer or reducing inflammation in a subject, wherein the method comprises administering a pharmaceutically effective amount of the recombinant, probiotic lactic acid bacterium of the present invention into the gastrointestinal tract of the subject, and wherein the cancer or inflammation is a cancer or inflammation of the gastrointestinal tract.

In some examples, there are provided the recombinant, probiotic lactic acid bacterium of the present invention for use in therapy. In some other examples, there are provided the recombinant, probiotic lactic acid bacterium of the present invention for use in treating cancer or reducing inflammation in a subject, wherein the cancer or inflammation is a cancer or inflammation of the gastrointestinal tract. In some other examples, there are provided use of the recombinant, probiotic lactic acid bacterium of the present invention in the manufacture of a medicament for treating cancer or reducing inflammation in a subject, wherein the cancer or inflammation is a cancer or inflammation of the gastrointestinal tract.

In some examples, the method of treating cancer or reducing inflammation in a subject can further comprise administering a pharmaceutically effective amount of immune checkpoint inhibitor. The administration of a pharmaceutically effective amount of immune checkpoint inhibitor can be administered either together or separately with the recombinant bacterium of the present invention. The term "immune checkpoint inhibitor" refers to a type of drug that blocks or inhibits checkpoint proteins. Checkpoint proteins are regulators of the immune system, and they keep immune responses from being too strong, which can sometimes prevent immune cells from killing cancer cells. When these checkpoint proteins are blocked, immune cells can target and/or eradicate cancer cells more effectively. Checkpoint proteins can be produced by cancer cells, or immune cells such as B-cells or T-cells. In some examples, the immune checkpoint inhibitor can be, but not limited to, inhibitors of programmed death ligand 1 (PDL-1), programmed death 1 (PD-1) and cytotoxic T lymphocyte-associated antigen-4 (CTLA-4).

In some examples, there are provided the recombinant, probiotic lactic acid bacterium of the present invention and an immune checkpoint inhibitor for use in therapy. In some other examples, there are provided the recombinant, probiotic lactic acid bacterium of the present invention and an immune checkpoint inhibitor for use in treating cancer or reducing inflammation in a subject, wherein the cancer or inflammation is a cancer or inflammation of the gastrointestinal tract. In some other examples, there are provided use of the recombinant, probiotic lactic acid bacterium of the present invention and an immune checkpoint inhibitor in the manufacture of a medicament for treating cancer or reducing inflammation in a subject, wherein the cancer or inflammation is a cancer or inflammation of the gastrointestinal tract.

The inventors also found that mice that have been treated with recombinant bacteria expressing Fnb without any tumor suppressor genes also showed reduction of tumour load. Thus, in one aspect, there is provided a method of treating cancer in a subject, wherein the method comprises administering a pharmaceutically effective amount of a recombinant, probiotic lactic acid bacterium, wherein the bacterium comprises a non-replicating plasmid vector comprising an adhesin gene operably linked to a promoter that directs expression of the adhesin gene in the bacterium. In one example, there is provided a method of treating cancer in a subject, wherein the method comprises administering a pharmaceutically effective amount of a recombinant, probiotic lactic acid bacterium, wherein the bacterium comprises a non-replicating plasmid vector comprising a gene encoding for an adhesin operably linked to a promoter that directs expression of the gene encoding for an adhesin in the bacterium.

The terms "treating" or its grammatical variants means to administer a composition to a subject or a system with an undesired condition or disease (e.g. cancer). The effect of the administration of the composition to the subject can be, but is not limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur.

The term "reduce" or "reduction" or grammatical variants thereof refer to a decrease in the specified parameter as compared to the same parameter of a reference. For example, in the context of "reducing inflammation", "reducing" refers to a decrease in the severity of inflammation, when compared to the severity of an untreated inflammation. In some examples, the severity of inflammation is reduced by at least 5%, at least 10%, at least 20%, at least 30%, at least 40%, at least 50%, at least 60%, at least 70%, at least 80%, at least 90% or at least 95% as compared to an untreated inflammation.

The term "inflammation" as used herein refers to a process by which the body's white blood cells and substances they produce protect the body from infection with foreign organisms, such as bacteria and viruses. The severity of inflammation can be measured by methods known in the art, such as blood tests which measures the level of fasting insulin, Hemoglobin A1C (HbA1c), C-Reactive Protein (CRP), serum ferritin and Red Blood Cell Width (RDW).

As used herein the term "pharmaceutically effective amount", "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being administered. The effect of the pharmaceutically effective amount can be relative to a control. Such controls are known in the art, and can be, for example the condition of the subject prior to or in the absence of administration of the drug, or drug combination, or in the case of drug combinations, the effect of the combination can be compared to the effect of administration of only one of the drugs. The pharmaceutically effective amount is determinable by means known in the art without undue experimentation, given the teachings contained herein. In some examples, the amount of bacteria should be sufficient to exert a tumor suppressing effect on the subject while still being avirulent to the subject. In some other example, the amount of bacteria should be sufficient to reduce inflammation in the subject while still being avirulent to the subject. The term "avirulent" as used herein refers to previously virulent organism that has been attenuated to a sufficient degree such that the administration of the attenuated organism to the animal host would not cause any detectable or measurable disease. Generally, such avirulence can be shown by a decrease in the LD50, the numbers of colonized organs, or the number of CFUs by a factor of 10, or a factor of 100, or by a factor of 1000 or more.

The pharmaceutically effective amount will depend upon the particular subject, the bacterial species, the type of cancer/inflammation involved, and the stage and/or severity of the cancer/inflammation. The dose and/or the dose frequency will also vary according to the age, body weight, and response of the individual subject. In general, the total daily dose range is from about $10^5$ to $10^{11}$ CFU (colony-forming unit) bacteria per day, or about $10^8$ to $5\times10^{10}$CFU bacteria per day, or about $2\times10^9$CFU bacteria per day in powder form or $9\times10^8$ to $1\times10^{10}$ CFU bacteria per day in liquid preparations, administered in single or divided doses. The length of time for a course of treatment should be at least 1 week, at least 2 weeks, at least 3 weeks, at least 4 weeks, at least 5 weeks, at least 7 weeks, at least 10 weeks, at least 13 weeks, at least 15 weeks, at least 20 weeks, at least 6 months, or at least 1 year. It may be necessary to use dosages outside these ranges in some cases as will be apparent to those skilled in the art. In certain examples, the recombinant bacteria can be administered for a period of time until the symptoms are under control, or when the disease has regressed partially or completely. Further, it is noted that the clinician or treating physician will know how and when to interrupt, adjust, or terminate use of the recombinant bacteria as a medicament in conjunction with individual patient response.

The term "CFU" as used herein refers to colony-forming unit, which is a unit used to estimate the number of viable bacteria or fungal cells in a sample. Viable is defined as the ability to multiply via binary fission under the controlled conditions. Counting with colony-forming units requires culturing the microbes and counts only viable cells, in contrast with microscopic examination which counts all cells, living or dead. In some examples, one CFU contains approximately $10^5$-$10^7$ cells.

Depending on the subject, the therapeutic benefits for cancer patients range from inhibiting or retarding the growth of the cancer and/or the spread of the cancer to other parts of the body (i.e., metastasis), palliating the symptoms of the cancer, improving the probability of survival of the subject with the cancer, prolonging the life expectancy of the subject, improving the quality of life of the subject, and/or reducing the probability of relapse after a successful course of treatment (e.g., surgery, chemotherapy or radiation). The effect of the bacteria of the invention on development and progression of cancer can be monitored by any methods known to one skilled in the art, including but not limited to measuring: a) changes in the size and morphology of the tumor using imaging techniques such as a computed tomographic (CT) scan or a sonogram; and b) changes in levels of biological markers of risk for cancer.

The term "Inhibit" or its grammatical variants as used herein means hinder or restrain a particular characteristic. It is understood that this is typically in relation to some standard or expected value, i.e., it is relative, but that it is not always necessary for the standard or relative value to be referred to. For example, "inhibits expression" means hindering, interfering with or restraining the expression or activity of a gene relative to a standard or a control. "Inhibits activity" can also mean to hinder or restrain the synthesis, expression or function of the gene product, such as a protein, relative to a standard or control.

The term "gastrointestinal tract" (or "GI tract" in short) as used herein refers to the organ system in animals, in particular mammalian animals, which takes in food, digests it to extract and absorb energy and nutrients, and expels the remaining waste. The GI tract consists of the oral cavity, esophagus, stomach, small intestine, large intestine, caecum, appendix, rectum, anus, liver and gall bladder.

Cancer of the GI tract refers to cancers that affect any part of the GI tract. Examples of cancer of the gastrointestinal tract include esophageal cancer, gastric cancer, colorectal cancer, pancreatic cancer, liver cancer, gallbladder & biliary tract cancer, and anal cancer. In one specific example, the cancer is colorectal cancer.

Colorectal cancer is cancer of the colon and rectum (or the large intestine), which is the last part of the gastrointestinal tract. When food enters the colon, water is absorbed and the food residue is converted into waste (faeces) by bacteria. The rectum is the terminal part of the colon that stores faeces before it is expelled through the anus. Polyps may form on the inner wall of the colon and rectum. These are benign lumps which are fairly common in people above the age of 50. However, certain types of polyps may develop into cancer. Colorectal cancer often has no symptoms at an early stage. The following signs may be indicated of colorectal cancer: blood in stools, change in bowel habits, abdominal pain or discomfort, anemia, and presence of a lump in the abdomen. Regular screening can detect polyps or colorectal cancer early. The following tests are commonly used, alone or in combination, to detect early stages of colorectal cancer: Faecal Immunochemical Test (FIT), colonoscopy, and flexible sigmoidoscopy. FIT is a preliminary test that detects the presence of small amounts of blood in faeces. Colonoscopy involves the examination of the colon and rectum using a flexible fibre-optic instrument introduced through the anus under sedation. In addition to its diagnostic use, a colonoscopy can be used for treatment, such as removing polyps, biopsying cancerous lumps, and staunching bleeding spots. Flexible sigmoidoscopy examines the internal lining of the lower end of the large intestine. A short, flexible, lighted tube is inserted into the rectum and slowly guided into the sigmoid colon.

The subject to be administered with the recombinant bacteria of the present invention can be any vertebrate, preferably a mammal, including domestic animals, sport animals, and primates, including humans.

The recombinant bacteria of the present invention can be administered to the gastrointestinal tract of the subject via any conventional routes of administration, including but not limited to, oral administration, administration by gastric feeding tube, administration by duodenal feeding tube, and rectal administration.

In some examples, oral administration is the preferred route of administration. The recombinant bacteria of the present invention can be administered orally alone. The recombinant bacteria can also be manufactured as an oral composition. Any dosage form may be employed for providing the subject with an effective dosage of the oral composition. Dosage forms include tablets, capsules, dispersions, suspensions, solutions, and the like. In some examples, compositions suitable for oral administration may be presented as discrete units such as capsules, cachets, or tablets, each containing a predetermined amount of the recombinant bacteria of the present invention, as a powder or granules or as a solution or a suspension in an aqueous liquid, a non-aqueous liquid, an oil-in-water emulsion, or a water-in-oil liquid emulsion. In general, the compositions are prepared by uniformly and intimately admixing the active ingredient with liquid carriers or finely divided solid carriers or both, and then, if necessary, shaping the product into the desired presentation.

The oral compositions may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art. The oral compositions may further contain additional ingredients, including but not limited to pharmaceutically acceptable carriers or excipients, vitamins, herbs (including traditional Chinese medicine products), herbal extracts, minerals, amino acids, flavoring agents, coloring agents, and/or preservatives. The recombinant bacteria can also be added to food which will be consumed by the subject. As known to those skilled in the relevant art, many methods may be used to mix the recombinant bacteria of the invention with food while the bacterial cells remain viable. In some examples, a culture broth comprising bacterial cells is added directly to food just prior to consumption. Dried powders of the bacterial cells can also be reconstituted and added directly to food just prior to consumption. Preferably, the recombinant bacteria of the invention are made and stored under conditions, such as temperature, from about 0° C. to 4° C. As used herein, the term "food" broadly refers to any kind of material, liquid or solid, that is used for nourishing an animal, and for sustaining normal or accelerated growth of an animal including humans. Many types of food products or beverages, such as but not limited to, fruit juice, herbal extracts, tea-based beverages, dairy products, soybean product, and rice products, can be used to form nutritional compositions comprising the recombinant bacteria of the invention.

Since the recombinant bacteria of the present invention are administered orally, the assistance of health professionals in administration of the bacteria is generally not essential.

In certain subjects, oral administration of the recombinant bacteria of the present invention may not be possible. In such circumstances, alternative administration routes such as administration by gastric feeding tube, administration by duodenal feeding tube, and rectal administration may be used. When such alternative administration routes are being used, it is preferred that the recombinant bacteria of the present invention be in the form of a liquid preparation.

Liquid preparations can take the form of solutions or suspensions, or they can be presented as a dry product for constitution with water or other suitable vehicle before use.

The temperature of the liquid used to reconstitute the dried product should in general be less than 65° C. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The recombinant bacteria of the present invention can be used in conjunction or in rotation with other types of treatment modalities, such as but not limited to surgery, chemotherapeutic agents, and radiation.

In preferred examples, the recombinant bacteria are live when being administered to the gastrointestinal tract of the subject. In some other examples, the recombinant bacteria are inactivated or dead when being administered to the gastrointestinal tract of the subject. The live recombinant bacteria can be either attenuated or un-attenuated. The term "attenuated" and its grammatical variants as used herein refers to the weakening or decreasing of the virulence of the wild-type organism. It follows that the term "un-attenuated" and its grammatical variants as used herein means that the virulence of the organism has not been weakened or decreased as compared to its wile-type organism. In some examples, when the bacteria of the *Lactococcus* genus are not virulent or harmful to its host organism, attenuation of the bacteria is not required.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

The following examples illustrate methods by which aspects of the invention may be practiced or materials that may be prepared which is suitable for the practice of certain embodiments of the invention.

EXAMPLE 1

Figure 2:
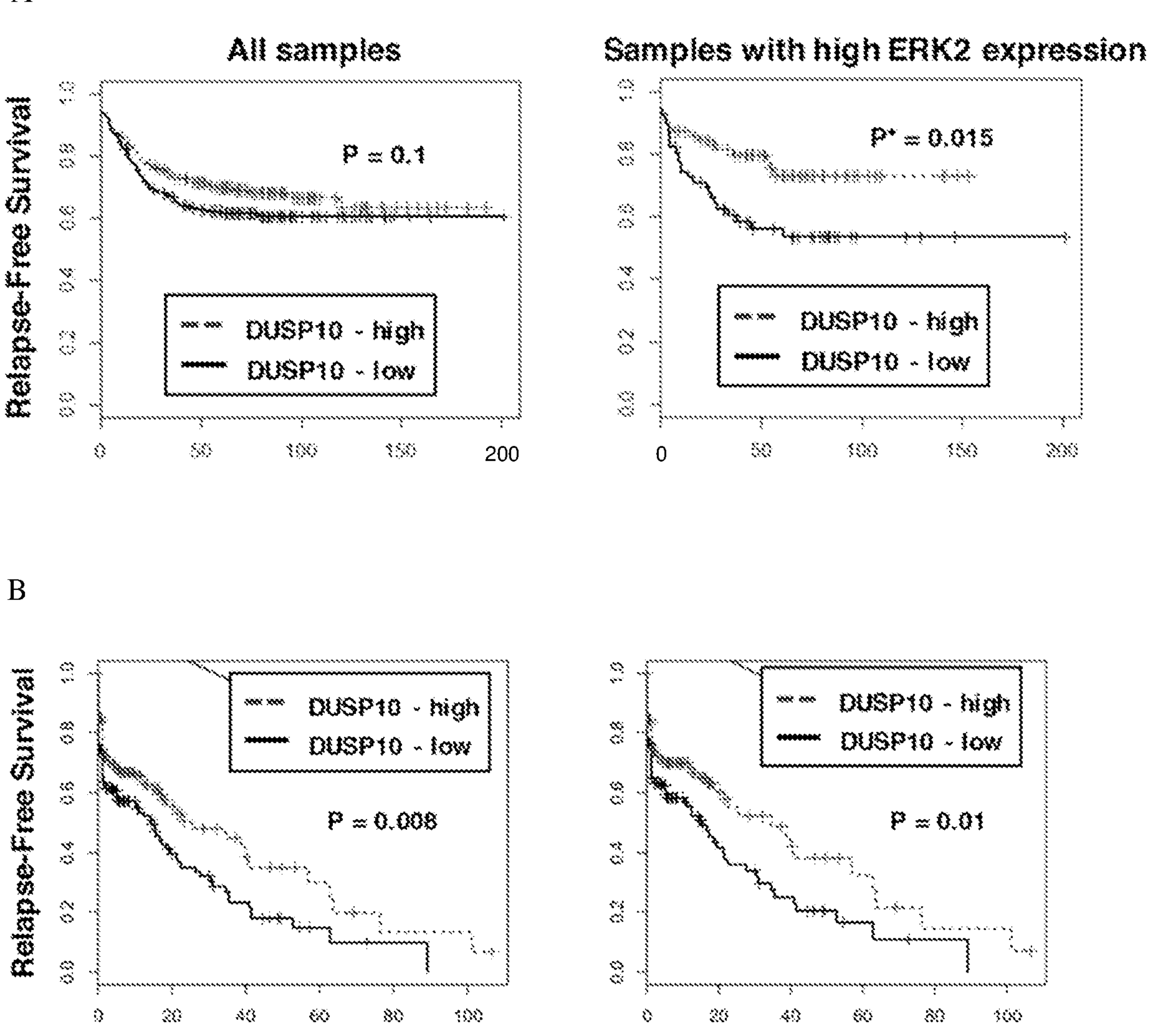
FIG. 2 shows results of survival data analysis using data available from Marisa L et al (FIG. 2A) and The Cancer Genome Atlas (FIG. 2B) based on Kaplan-Meier method. The Y-axis in each graph represents the probability of relapse-free survival (RFS), and the X-axis in each graph represents the survival time in months. RFS probability in patient cohort from Marisa L et al. trended marginally higher (P=0.1) for patients with tumour that had high DUSP10 expression (FIG. 2A left panel). After sample stratification for ERK expression, it was found that high DUSP10 in tumours was associated with approximately 20% improvement in survival probability of patients with high ERK expression (FIG. 2A right panel). Improvement in patient survival was more striking in the TCGA cohort (FIG. 2B). Survival of patients with high DUSP10 expression was increased by approximately 20% up to 60 months with or without ERK2 stratification. Together, the data in FIG. 2 suggests that DUSP10 expression may be functionally important for control of tumour development that resulted in better survival in the patients.

High DUSP10 Expression is Associated with Better Overall Survival in CRC Patients Recently, an increasing number of studies have shown that dysregulation of DUSPs expression was associated with multiple cancers, and altered function of DUSPs was often reported in association with altered MAPK activities in the tumour. A detailed analysis of published CRC survival datasets from Marisa L et al. (PLoS Med. 2013. 10, e1001453) and The Cancer Genome Atlas (TCGA) (Nature 2012. 487, 330-337) was carried out to examine the plausible relationship between DUSP10 levels and CRC patients' survival. As shown in FIG. 2, relapse free survival (RFS) probability in patient cohort from Marisa L et al. trended marginally higher (P=0.1) for patients with tumour that had high DUSP10 expression (FIG. 2A, left panel). After sample stratification for ERK expression, it was found that high DUSP10 in tumours was associated with approximately 20% improvement in survival probability of patients with high ERK expression (FIG. 2B, right panel). Improvement in patient survival was more striking in the TCGA cohort (FIG. 2B). Survival of patients with high DUSP10 expression was increased by approximately 20% for up to 60 months with or without ERK2 stratification. Together, these data suggest that DUSP10 expression may be functionally important for control of tumour development that resulted in better survival in the patients.

EXAMPLE 2

Figure 3:
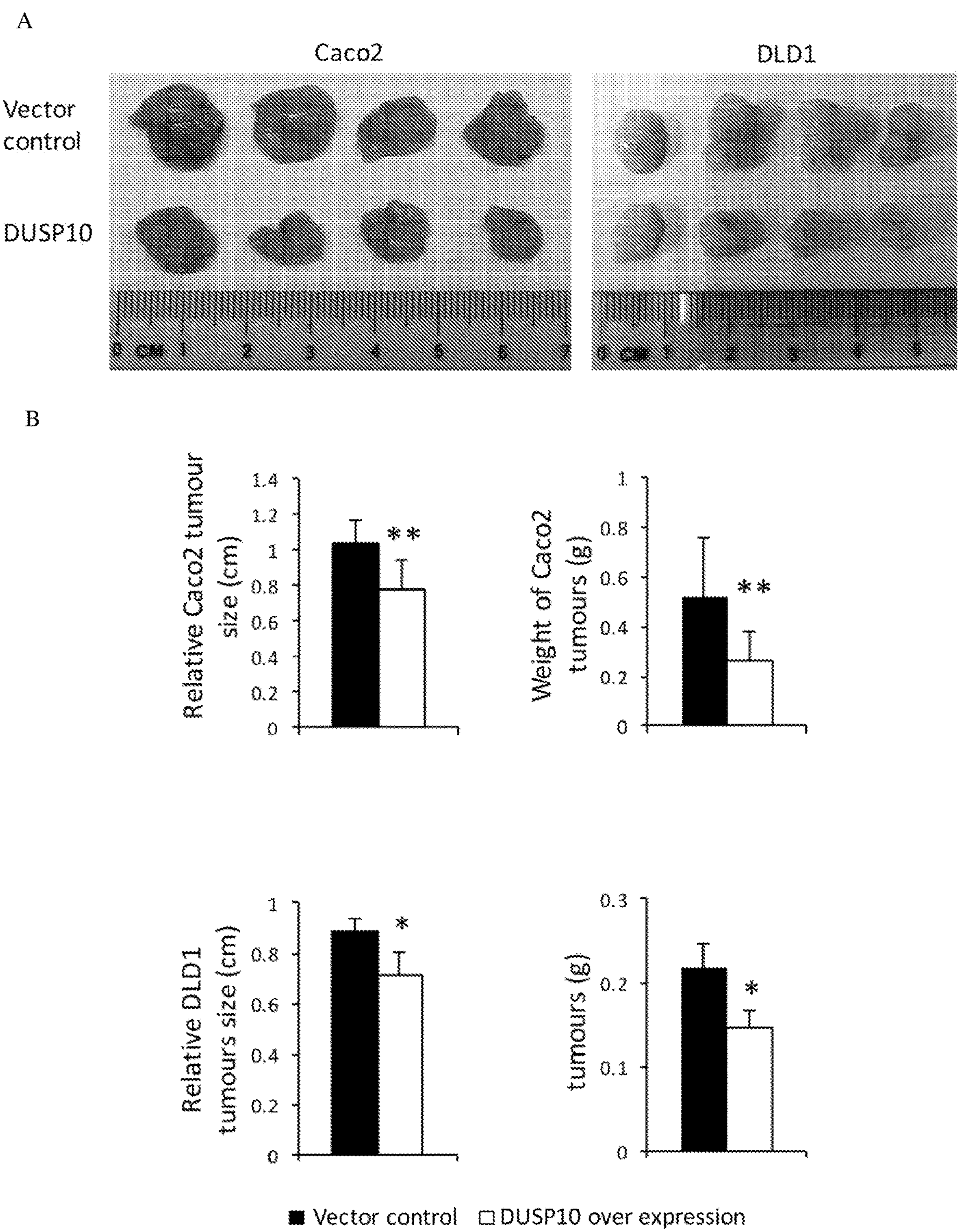
FIG. 3 shows effects of DUSP10 over expression on the growth of Caco2 and DLD1 xenograft tumours.
Figure 4:
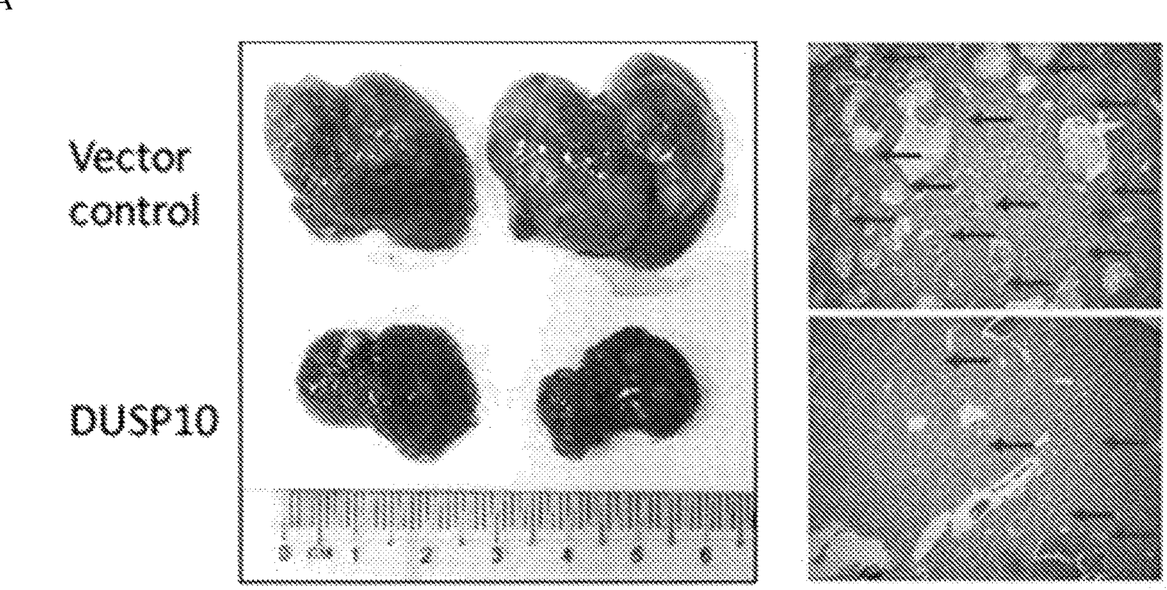
FIG. 4 shows the effects of of DUSP10 over expression on metastatic colonisation of HCT116 cells to the liver in an intra-splenic injection mouse model.
Figure 4:
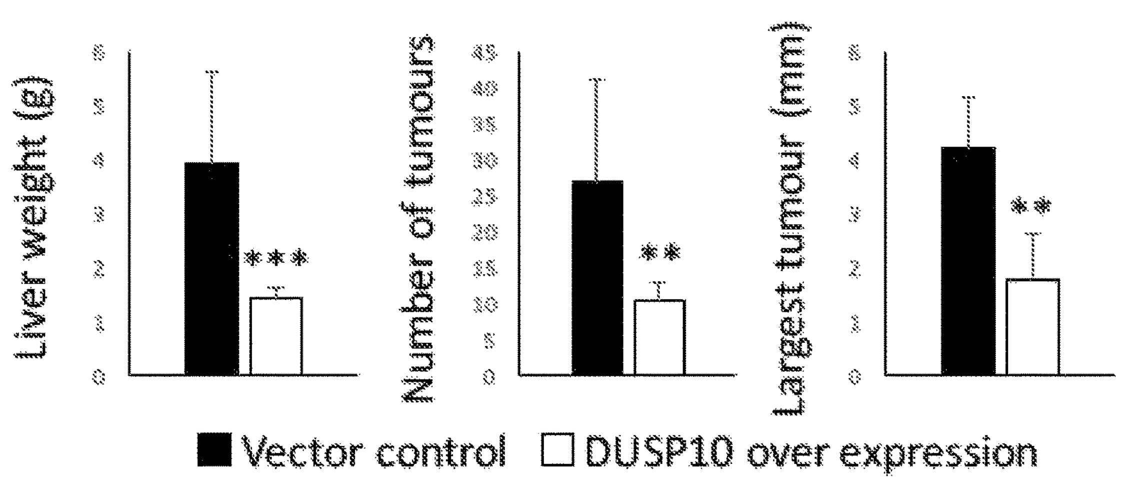

DUSP10 Overexpression in Human CRC Cells Supressed Cancer Cell Growth and Metastasis To confirm the tumour suppression function of DUSP10, human CRC cell lines Caco2 and DLD1 that stably overexpressing DUSP10 were generated for engraftment as tumour xenografts in immunocompromised mice. Results showed that DUSP10 overexpression reduced tumour growth in vivo (FIG. 3). A key difference between the two cell lines is the presence of KRAS mutation (G13D) in DLD1, whereas wildtype KRAS is found in Caco2. This suggest that overexpression of DUSP10 may be effective for suppression of tumour cell growth regardless of the KRAS status. Interestingly, overexpression of DUSP10 in HCT116 human CRC cells harbouring Kras mutation (G13D) resulted in reduced metastasis to the liver (FIG. 4). In this experiment, HCT116 cells overexpressing DUSP10 or the control vector were injected into the spleen of immunocompromised NSGS mice for metastasis to occur over 3 weeks. There were approximately two-fold less macroscopic metastatic lesions of smaller size in the liver of mice injected with DUSP10 overexpressed HCT116 cells. KRAS is one of the most commonly mutated gene that results in resistance to drug therapy and subsequent increased ERK1/2 activation and cellular proliferation. Hence, the findings above demonstrated the potential of DUSP10 overexpression therapy for both KRAS wildtype and mutant tumours and possibility of reduction in metastatic disease progression.

EXAMPLE 3

Development of Fibronectin-Binding Protein Expressing *L. lactis* for the Delivery of DUSP10 Expression Plasmid (*L. Lactis*-Fnb-DUSP10)

Figure 5:
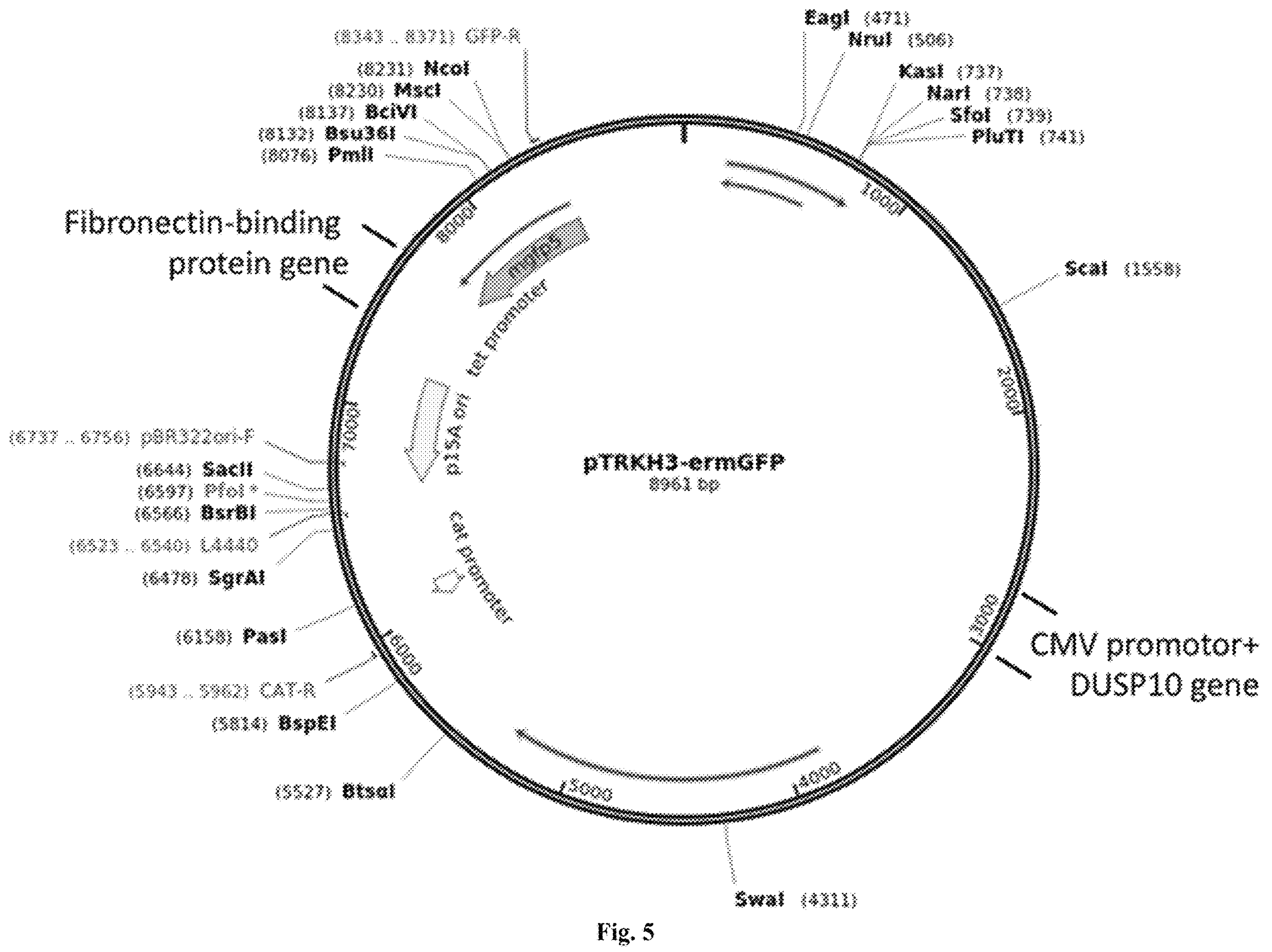
FIG. 5 depicts a schematic diagram showing DNA construct developed for transformation into *L. lactis* for expression of bacterial fibronectin-binding protein (derived from S. aureus) and human DUSP10 (not drawn to scale).

DNA plasmid harbouring the gene insert for (1) *S. aureus* derived fibronectin-binding protein (Fnb) and (2) human DUSP10 was constructed by modifying the vector backbone, pTRKH3-ermGFP (Addgene) (FIG. 5). The resultant DNA plasmid was transformed into *Lactococcus lactis* (ATCC) by electroporation and selected based on erythromycin resistance. Single, positive clone was subsequently isolated and stored in 20% sterile glycerol until required for use. For all subsequent infection experiments, three different controls were implemented including untreated group, a group that was infected with *L. lactis* harbouring the vector backbone ("*Lactis*-vect") and *L. lactis* harbouring the vector backbone with Fnb gene insert only (*Lactis*-Fnb).

EXAMPLE 4

Reduction in Tumour Cell Growth In Vitro and In Vivo After Treatment with *L. Lactis*-Fnb-DUSP10

Figure 6:
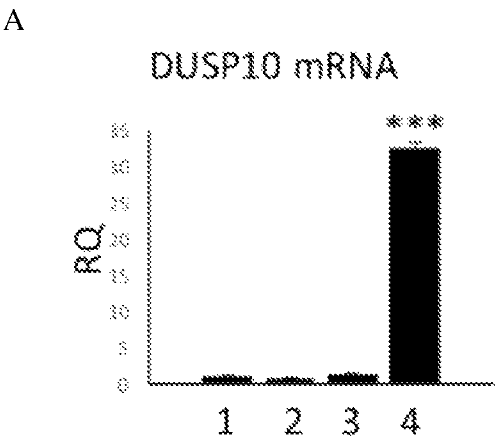
FIG. 6 shows the effects of *L. lactis*-Fnb-DUSP10 infection in Caco2 cells.
Figure 6:
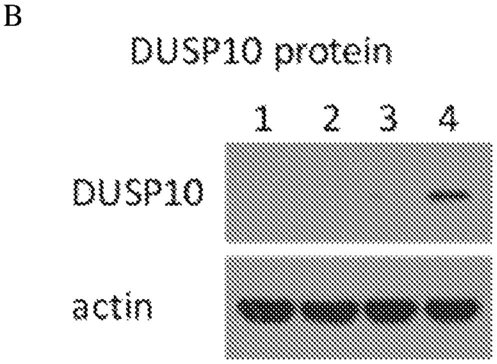
Figure 6:
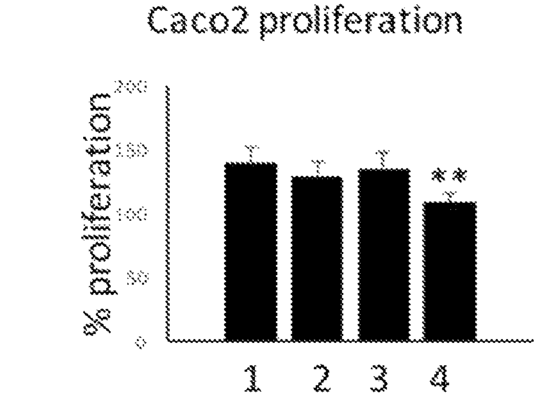
Figure 7:
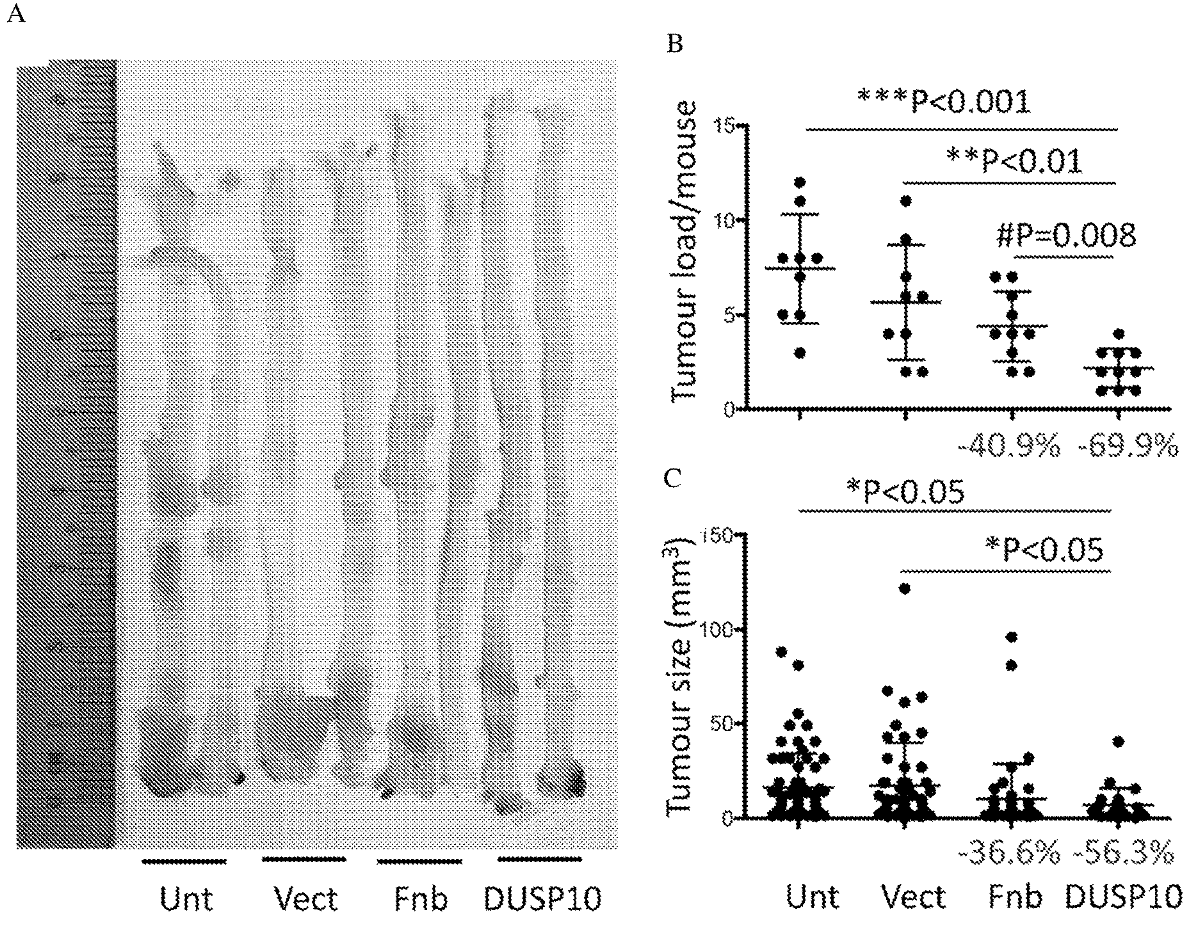
FIG. 7 shows the effects of *L. lactis*-Fnb-DUSP10 on colon tumour load in mice.
Figure 8:
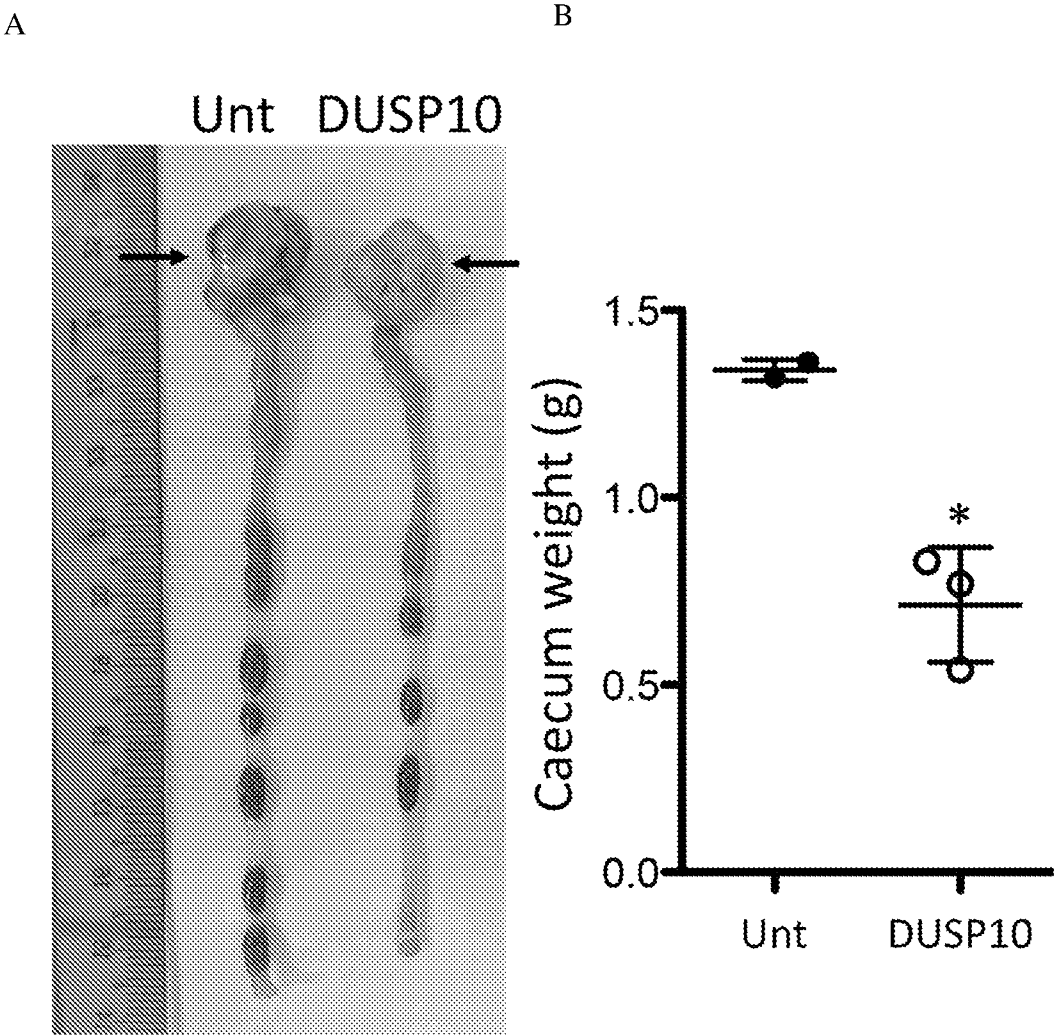
FIG. 8 shows the effect of *L. lactis*-Fnb-DUSP10 on caecal transplanted Ls174T tumour growth.

In order to determine the functionality of *L. Lactis*-Fnb-DUSP10 in vitro, Caco2 (human CRC cell line) was used for infection with *L. Lactis*-Fnb-DUSP10 or controls (MOI: 1500). As shown in FIG. 6, at 24 hours post infection, both mRNA and protein levels of DUSP10 were increased in Caco2 cells infected with *L. Lactis*-Fnb-DUSP10. Functionally, a 20% reduction in Caco2 proliferation was detected after 3 days of daily infection with *L. Lactis*-Fnb-DUSP10 compared to control uninfected cells (FIG. 6*c*). More importantly, daily treatment through oral gavage of *L. Lactis*-Fnb-DUSP10 (dose=$1.5\times10^9$ CFU bacteria) for 7 weeks had successfully suppressed intestinal tumour development in the AOM/DSS induced CRC mouse model (FIG. 7). Tumour load in mice given *L. Lactis*-Fnb-DUSP10 was reduced by ~70% and ~60% compared to untreated mice and mice treated with *Lactis*-vect. Interestingly, mice given *Lactis*-Fnb also showed ~41% reduction of tumour load, which needs further examination (this may due to the slight induction of DUSP10 after *Lactis*-Fnb treatment—see FIG. 6*b*). Nevertheless, *L. Lactis*-Fnb-DUSP10 further enhanced the tumour suppression effect by another ~30%. In addition, overall tumour size was −56% smaller in mice treated with *L. Lactis*-Fnb-DUSP10. The efficacy of *L. Lactis*-Fnb-DUSP10 was also determined using a human CRC cell line transplant model. In this pilot experiment, $3\times3$ $mm^2$ human Ls174T tumour xenografts were transplanted and established in the caecum of immunocompromised mice for 2 weeks before treatment with *L. Lactis*-Fnb-DUSP10 by oral gavage. As shown in FIG. 8, the size of the transplanted Ls174T xenografts was smaller in mice treated with *L. Lactis*-Fnb-DUSP10 for 2 weeks. These in vivo results demonstrated that *L. Lactis*-Fnb-DUSP10 therapy is highly promising with potential to be integrated with current CRC treatment and should be develop for clinical application.

EXAMPLE 5

Reduction in Colonic Inflammation In Vivo After Treatment with *L. Lactis*-Fnb-DUSP10

Figure 9:
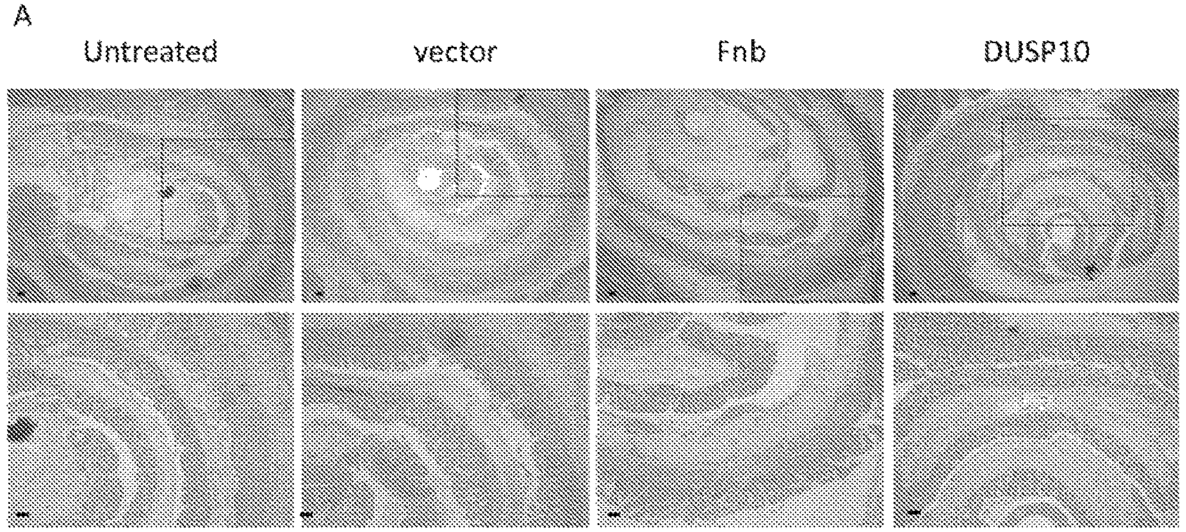
FIG. 9 shows the effects of *L. lactis*-Fnb-DUSP10 treatment in mice with colonic inflammation.
Figure 9:
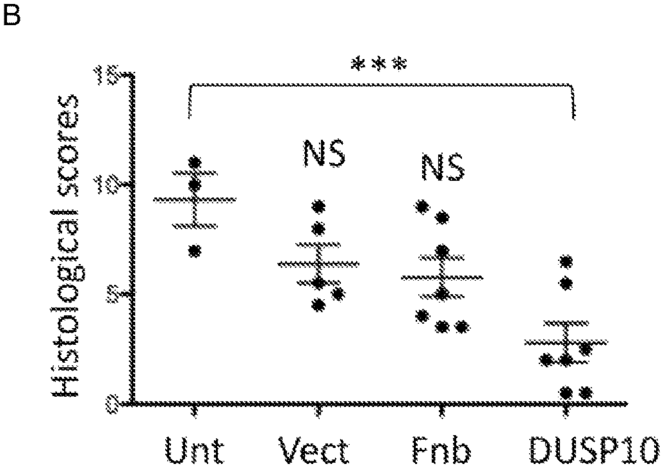
Figure 9:
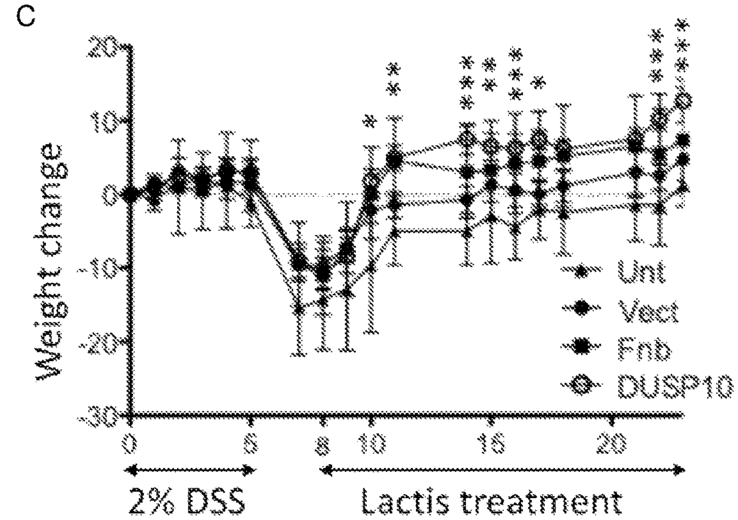
Figure 9:
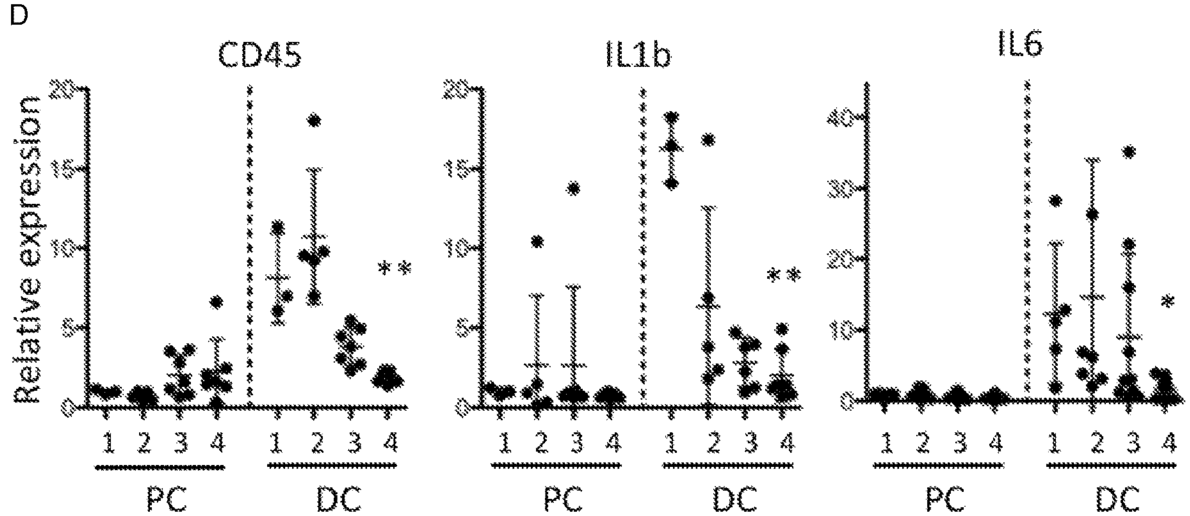

Mice were given 2% DSS (Dextran sulfate sodium) to induce colonic inflammation before initiation of *L. lactis*-Fnb-DUSP10 treatment. Different treatments (*L. lactis* with vector control; *L. lactis*-Fnb and *L. lactis*-Fnb-DUSP10) were administered to the mice. As shown in FIG. 9, treating with *L. lactis*-Fnb-DUSP10 has significantly reduced colonic inflammation as compared to the control groups.

EXAMPLE 6

Reduction in Tumour Cell Growth In Vitro and In Vivo After Combination Treatment with *L. Lactis*-Fnb-DUSP10 and Anti-PDL-1

Figure 10:
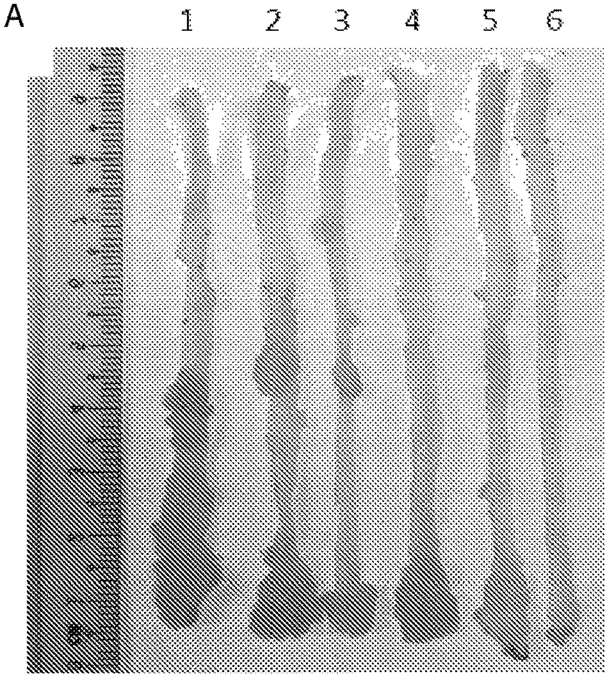
FIG. 10 shows the effects of *L. lactis*-Fnb-DUSP10 and/or anti-PDL-1 treatment on colon tumour load in mice.
Figure 10:
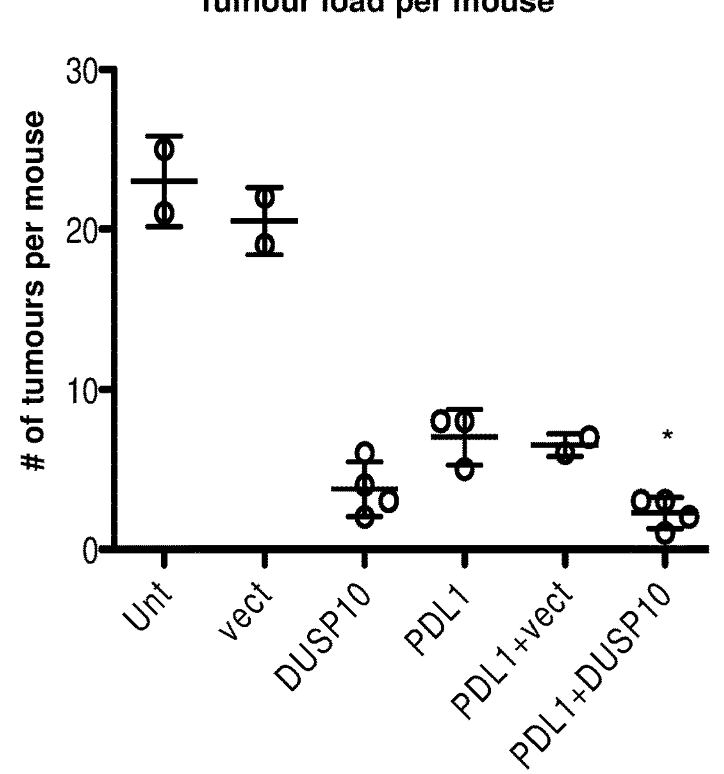

In order to determine whether *L. Lactis*-Fnb-DUSP10 can be used in combination with immune checkpoint inhibitors to treat cancer, mice were treated with a combination of *L. Lactis*-Fnb-DUSP10 and anti-PDL-1. Ten-week old mice were given a single dose of 10mg/kg azoxymethane (AOM) (Sigma Aldrich; Mo., USA) via intra-peritoneal injection to induce colon tumours. The mice were allowed to rest for one week before they were subjected to 3 cycles of 1% DSS administration for five days with two weeks rest. After 16 weeks post AOM injection, the mice were subjected to the initiation of daily treatments with *L. Lactis* and/or anti-PDL-1 (*L. lactis* with vector control; *L. lactis*-Fnb-DUSP10, anti-PDL-1, anti-PDL-1+*L. lactis*-vector and anti-PDL-1+*Lactis*-Fnb-DUSP10) for 4 weeks before the mice were sacrificed and tumour load was determined. Tumour load in mice given anti-PDL-1 and anti-PDL-1+*L. lactis*-vector were reduced by ~68% and ~70% compared to untreated mice and mice treated with *L. lactis*-vector. Tumour load in mice treated with *L. Lactis*-Fnb-DUSP10 were reduced by ~83%. Interestingly, mice given anti-PDL-1+*Lactis*-Fnb-DUSP10 showed the greatest effect, wherein there is ~90% reduction in tumour load (FIG. 10*b*). This shows that the anti-tumour effects of *Lactis*-Fnb-DUSP10 can be further enhanced when used in combination with an immune checkpoint inhibitor.

Description of SEQ ID

Table 2 below details SEQ ID NOs referenced herein and their corresponding sequences that are not mentioned in Table 1. A brief description of the sequences is also provided.

| SEQ ID NO: | Description | Sequence |
|---|---|---|
| 1 | DUSP10 gene | ATGCCTCCGTCTCCTTTAGACGACAGGGTAGTAGTGGCA<br>CTATCTAGGCCCGTCCGACCTCAGGATCTCAACCTTTGTT<br>TAGACTCTAGTTACCTTGGCTCTGCCAACCCAGGCAGTAA<br>CAGCCACCCTCCTGTCATCGCCACCACCGTTGTGTCCCTC<br>AAGGCTGCGAATCTGACGTATATGCCCTCATCCAGCGGC<br>TCTGCCCGCTCGCTGAATTGTGGATGCAGCAGTGCCAGCT<br>GCTGCACTGTGGCAACCTACGACAAGGACAATCAGGCCC<br>AAACCCAAGCCATTGCCGCTGGCACCACCACCACTGCCA<br>TCGGAACCTCTACCACCTGCCCTGCTAACCAGATGGTCA<br>ACAATAATGAGAATACAGGCTCTCTAAGTCCATCAAGTG<br>GGGTGGGCAGCCCTGTGTCAGGGACCCCCAAGCAGCTAG<br>CCAGCATCAAAATAATCTACCCCAATGACTTGGCAAAGA<br>AGATGACCAAATGCAGCAAGAGTCACCTGCCGAGTCAGG<br>GCCCTGTCATCATTGACTGCAGGCCCTTCATGGAGTACAA<br>CAAGAGTCACATCCAAGGAGCTGTCCACATTAACTGTGC<br>CGATAAGATCAGCCGGCGGAGACTGCAGCAGGGCAAGA<br>TCACTGTCCTAGACTTGATTTCCTGTAGGGAAGGCAAGG<br>ACTCTTTCAAGAGGATCTTTTCCAAAGAAATTA<br>TAGTTTATGATGAGAATACCAATGAACCAAGCCGAGTGA<br>TGCCCTCCCAGCCACTTCACATAGTCCTCGAGTCCCTGAA<br>GAGAGAAGGCAAAGAACCTCTGGTGTTGAAAGGTGGACT<br>TAGTAGTTTTAAGCAGAACCATGAAAACCTCTGTGACAA<br>CTCCCTCCAGCTCCAAGAGTGCCGGGAGGTGGGGGGCGG<br>CGCATCCGCGGCCTCGAGCTTGCTACCTCAGCCCATCCCC<br>ACCACCCCTGACATCGAGAACGCTGAGCTCACCCCCATC<br>TTGCCCTTCCTGTTCCTTGGCAATGAGCAGGATGCTCAGG<br>ACCTGGACACCATGCAGCGGCTGAACATCGGCTACGTCA<br>TCAACGTCACCACTCATCTTCCCCTCTACCACTATGAGAA<br>AGGCCTGTTCAACTACAAGCGGCTGCCAGCCACTGACAG<br>CAACAAGCAGAACCTGCGGCAGTACTTTGAAGAGGCTTT<br>TGAGTTCATTGAGGAAGCTCACCAGTGTGGGAAGGGGCT<br>TCTCATCCACTGCCAGGCTGGGGTGTCCCGCTCCGCCACC<br>ATCGTCATCGCTTACTTGATGAAGCACACTCGGATGACC<br>ATGACTGATGCTTATAAATTTGTCAAAGGCAAACGACCA<br>ATTATCTCCCCAAACCTTAACTTCATGGGGCAGTTGCTAG<br>AGTTCGAGGAAGACCTAAACAACGGTGTGACACCGAGA<br>ATCCTTACACCAAAGCTGATGGGCGTGGAGACGGTTGTG<br>TGA |
| 7 | Fibronectin-binding protein A (FnBPA) gene | GCATTTAAAGGGAGATATTATAGTGAAAAACAATCTTAG<br>GTACGGCATTAGAAAACATAAATTGGGAGCAGCATCAGT<br>ATTCTTAGGAACAATGATCGTTGTTGGGATGGGACAAGA<br>TAAAGAAGCTGCAGCATCAGAACAAAAGACAACTACAG<br>TAGAAGAAAATGGGAATTCAGCTACTGATAATAAAGTAA<br>ACGAAACACAAACAACTACAACTAACGTTAATACTATAG |

-continued

| SEQ ID NO: | Description | Sequence |
| --- | --- | --- |
| | | ATGAAACACAATCATACAGCGCAACAGCAACAGAACAA CCGTCAAACGCAACACAAGTAACAACTGAAAAAGCACC AAAAGCAGTACAAGCACCACAAACTGCACAACCAGCAA ATGTAGAAACAGTTAAAGAAGAGGTAGTTAAGGAAGAA GCGAACCCTCAAGTTAAGGAAACGACACAATCTCAAGAC AATAGCGGAGATCAAAGACAAGTAGATTTAACACCTAAA AAGGCTACACAAAATCAAGCAGCAGAAACACAAGTTGA AGTGGCACAGCCAAGAACGGTATCAGAAAGTAAACCAC GTGTGACAAGATCAGCAGATGTAGCGGAAGCTAAGGAA GCTAGTGACGCGAAAGTGGAAACGGGTACAGATGTGAC AAGTAAAGTTACAGTGGAAAGTGGTTCTATTGAGGCACC TCAAGGAAATAAAGTAGAGCCACATGCTGGTCAACGTGT CGTACTGAAATACAAATTGAAATTCGAAAAGGGTTTACA CAAAGGAGATTATTTTGATTTCACCTTGTCTAATAATGTA AATACTTATGGAGTTTCAACAGCTAGAAAAGTACCAGAA ATCAAAAATGGTTCAGTCGTAATGGCGACAGGTCAACTT CTTGGAAATGGGAAAATTAGGTATACATTTACAGACTAT ATTGATTATAAAGTAAATGTGACTGCTGATTTAGAAATC AATTTATTTATTGATCCTAAAACTGTACAAAGCAATGGAC AACAAACAATAACTTCAACGTTGAATGATAAGGAAACAA AAAACACATTGCCAATAGAATATAATCCAGGAGTAAGTA ATAGCTATGCTAATGTAAATGGATCTATTGAAACTTTTGA TAAAGGGAACAATAAATTCACTCATGTAGCTTACATAAA ACCACAAAATGGGCATAAATCAGATAGCGTTTCAATTAC TGGTACACTAACTCAAGGTAGCAAAGCTAATGGAAATGT TCCAACTGTAAAAGTATATGAAGTCTTAAAGGATGCTAA AGAATTACCAGAAAGTGTATATGCAAACATATCAGACTC TACAATGTTTAAAGATGTAACTCAGGAAATGAAAGATAA ATTAAAAGTAGAAAATAATGGGAGTTATAAATTAGACAT TGAGAAATTAGAAAAAAGTTATGTTATACACTATGATGG TGAATACTTAAGTGGTTCAGATCAAGTGAATTTTAGAAC GCATATGTTTGGATATCCAGAACAGCAGTATAAGTACTA CTATACTCATTTGGGATACCAACTTACATGGGATAATGG ATTAGTTTTATATAGTAACAAAGCAAAAGGTGATGGAAC GAATGGAACAATAACAGAATCGAATAATATGACATTTGA TGAAGAATATGGAACTGGAGTTATTACAGGTCAATATGA TAAGAATTTAGTAACTACTGTTGAAGAAGAATATGATTC TTCAACTCTTGACATTGATTACCACACAGCTATAGATGGT GAAGGTGGTTATGTTGATGGATACATTGAAACAATAGAA GAAACGGATTCATCAGCTATTGATATCGATTACCATACTG CTGTGGATAGCGAAGCGGGTCACGTTGGAGGATACACTG AGTCCTCTGAGGAATCAAATCCAATTGACTTTGAAGAAT CTACGCATGAAAATTCAAAACATCACGCTGATGTTGTTG AATATGAAGAGGATACAAACCCAGGTGGTGGTCAGGTTA CTACTGAGTCTAACTTAGTTGAATTTGACGAAGAGTCTAC AAAAGGTATTGTAACTGGCGCAGTGAGCGACCATACAAC AATTGAAGATACGAAAGAATATACAACTGAAAGTAATCT GATTGAACTAGTAGATGAACTACCTGAAGAACATGGTCA AGCACAAGGACCAATCGAGGAAATTACTGAAAACAATC ATCATATTTCTCATTCTGGTTTAGGAACTGAAAATGGTCA CGGTAATTATGGTGTGATTGAAGAAATCGAAGAAAATAG CCATGTTGATATTAAGAGTGAATTAGGTTATGAAGGTGG CCAAAATAGCGGTAACCAGTCATTCGAGGAAGACACAGA AGAAGATAAACCTAAATATGAACAAGGTGGCAATATCGT AGATATCGATTTCGATAGTGTACCTCAAATTCATGGTCAA AATAAAGGTGATCAGTCATTCGAAGAAGATACAGAGAA AGACAAACCTAAGTATGAACAAGGTGGTAATATCATTGA TATCGACTTCGACAGTGTGCCACAAATTCATGGATTCAAT AAGCATAATGAAATTATTGAAGAAGATACAAACAAAGAT AAACCAAATTATCAATTCGGTGGACACAACATTGTTGAT TTTGAAGAAGATACACTTCCGAAAGTAAGCGGTCAAAAT GAAGGTCAACAAACGATTGAAGAAGATACAACGCCGCC AACGCCACCGACACCAGAAGTACCGAGTGAGCCGGAAA CACCAACACCACCGACGCCGGAAGTACCGAGTGAGCCAG AAACACCAACGCCACCGACACCAGAAGTACCAAGTGAG CCGGAAACACCAACACCGCCAACACCAGAGGTACCAAGT GAGCCGGAAACACCAACACCGCCAACACCAGAGGTACC AGTTGAACCTGGTAAACCAGTACCACCTGCTAAAGAAGA ACCTAAAAAACCTTCTAAACCAGTGGAACAAGGTAAAGT AGTAACACCTGTTATTGAAATCAATGAAAAGGTTAAAGC AGTGGCACCAACTAAACAAAAACAATCTAAGAAATCTGA ACTACCTGAAACAGGTGGAGAAGAATCAACAAACAAAG GTATGTTGTTCGGCGGATTATTCAGCATTCTAGGTTTAGC GTTATTACGTAGAAATAAAAAGAATAACAAAGCATAATT AACAAAAATTGACGGGTTTATTTCATAAATTACATGAAG TAAGCCTGTTTTTTTATATTAAATCAAATTTTTAATAGA |

-continued

| SEQ ID NO: | Description | Sequence |
|---|---|---|
| | | AAATTAGAGTGTTTTCTGATTGCTTCATTGGTTTATGTCT<br>GATGATTGATAACGAACTGAGAGATAAAGTTAGAATTTT<br>AAACTAGT |
| 8 | erm promoter | CGGTATCGATAAGCTTAGTCTAGAATCGATACGATTTTGA<br>AGTGGCAACAGATAAAAAAAAGCAGTTTAAAATTGTTGC<br>TGAACTTTTAAAACAAGCAAATACAATCATTGTCGCAAC<br>AGATAGCGACAGAGAAGGCGAAAACATTGCCTGGTCGAT<br>CATTCATAAAGCAAATGCCTTTTCTAAAGATAAAACGTA<br>TAAAAGACTATGGATCAATAGTTTAGAAAAAGATGTGAT<br>CCGTAGCGGTTTTCAAAATTTGCAACCAGGAATGAATTA<br>CTATCCCTTTTATCAAGAAGCGCACAAAAAGAAAAACGA<br>AATGATACACCAATCAGTGCAAAAAAAGATATAATGGGA<br>GATAAGACGGTTCGTGTTCGTGCTGACTTGCACCATATCA<br>TAAAAATCGAAACAGCAAAGAATGGCGGAAACGTAAAA<br>GAAGTTATGGAAATAAGACTTAGAAGCAAACTTAAGAGT<br>GTGTTGATAGTGCAGTATCTTAAAATTTTGTATAATAGGA<br>ATTGAAGTTAAATTAGATGCTAAAAATTTGTAATTAAGA<br>AGGAGTGAATT |
| 9 | nisin promoter | CTCCTGTTTTACAACCGGGTGTACATAGCGAAATACTTGT<br>AATGCGTGGTGATGCACCTGAATCTTTCTTCGAAACAGAT<br>ACCAAATCCAAGCTAAAATCTTTTGTACTCATTTTGAGTG<br>CCTCCTTATAATTTATTTTGTAGTTCCTTCGAACGAAATC<br>ATTGTATCTAACAAACTTCAGAATTTAATCAGAGCCGTTT<br>ATTATGCTCGCGTTATCGACAATAATATTATTACCAATAC<br>TTTCTCAAGATAGAATTAAGACTGTTTTAGATTTGTTAAT<br>GTTTCTATTGTCAGTATAGTTATAAGACT |
| 10 | DUSP10 protein | MPPSPLDDRVVVALSRPVRPQDLNLCLDSSYLGSANPGSNS<br>HPPVIATTVVSLKAANLTYMPSSSGSARSLNCGCSSASCCTV<br>ATYDKDNQAQTQAIAAGTTTTAIGTSTTCPANQMVNNNEN<br>TGSLSPSSGVGSPVSGTPKQLASIKIIYPNDLAKKMTKCSKS<br>HLPSQGPVIIDCRPFMEYNKSHIQGAVHINCADKISRRRLQQ<br>GKITVLDLISCREGKDSFKRIFSKEIIVYDENTNEPSRVMPSQ<br>PLHIVLESLKREGKEPLVLKGGLSSFKQNHENLCDNSLQLQE<br>CREVGGGASAASSLLPQPIPTTPDIENAELTPILPFLFLGNEQ<br>DAQDLDTMQRLNIGYVINVTTHLPLYHYEKGLFNYKRLPA<br>TDSNKQNLRQYFEEAFEFIEEAHQCGKGLLIHCQAGVSRSA<br>TIVIAYLMKHTRMTMTDAYKFVKGKRPIISPNLNFMGQLLE<br>FEEDLNNGVTPRILTPKLMGVETVV |
| 11 | Fibronectin-binding protein B (FnBPB) gene | GTGAAAAGCAATCTTAGATACGGCATAAGAAAACACAA<br>ATTGGGAGCGGCCTCAGTATTCTTAGGAACAATGATCGT<br>TGTTGGAATGGGACAAGAAAAAGAAGCTGCAGCATCGG<br>AACAAAACAATACTACAGTAGAGGAAAGTGGGAGTTCA<br>GCTACTGAAAGTAAAGCAAGCGAAACACAAACAACTAC<br>AAATAACGTTAATACAATAGATGAAACACAATCATACAG<br>CGCGACATCAACTGAGCAACCATCACAATCAACACAAGT<br>AACAACAGAAGAAGCACCGAAAACTGTGCAAGCACCAA<br>AAGTAGAAACTTCGCGAGTTGATTTGCCATCGGAAAAAG<br>TTGCTGATAAGGAAACTACAGGAACTCAAGTTGACATAG<br>CTCAACCAAGTAACGTCTCAGAAATTAAACCAAGAATGA<br>AAAGATCAACTGACGTTACAGCAGTTGCAGAGAAAGAA<br>GTAGTGGAAGAAACTAAAGCGACAGGTACAGATGTAAC<br>AAATAAAGTGGAAGTAGAAGAAGGTAGTGAAATTGTAG<br>GACATAAACAAGATACGAATGTTGTAAATCCTCATAACG<br>CAGAAAGAGTAACCTTGAAATATAAATGGAAATTTGGAG<br>AAGGAATTAAGGCGGGAGATTATTTTGATTTCACATTAA<br>GCGATAATGTTGAAACTCATGGTATCTCAACACTGCGTA<br>AAGTTCCGGAGATAAAAAGTACAGATGGTCAAGTTATGG<br>CGACAGGAGAAATAATTGGAGAAAGAAAAGTTAGATAT<br>ACGTTTAAAGAATATGTACAAGAAAAGAAAGATTTAACT<br>GCTGAATTATCTTTAAATCTATTTATTGATCCTACAACAG<br>TGACGCAAAAAGGTAACCAAAATGTTGAAGTTAAATTGG<br>GTGAGACTACGGTTAGCAAAATATTTAATATTCAATATTT<br>AGGTGGAGTTAGAGATAATTGGGGAGTAACAGCTAATGG<br>TCGAATTGATACTTTAAATAAAGTAGATGGGAAATTTAG<br>TCATTTTGCGTACATGAAACCTAACAACCAGTCGTTAAGC<br>TCTGTGACAGTAACTGGTCAAGTAACTAAAGGAAATAAA<br>CCAGGGGTTAATAATCCAACAGTTAAGGTATATAAACAC<br>ATTGGTTCAGACGATTTAGCTGAAAGCGTATATGCAAAG<br>CTTGATGATGTCAGCAAATTTGAAGATGTGACTGATAAT<br>ATGAGTTTAGATTTTGATACTAATGGTGGTTATTCTTTAA<br>ACTTTAATAATTTAGACCAAAGTAAAAATTATGTAATAA<br>AATATGAAGGGTATTATGATTCAAATGCTAGCAACTTAG |

-continued

| SEQ ID NO: | Description | Sequence |
|---|---|---|
| | | AATTTCAAACACACCTTTTTGGATATTATAACTATTATTA<br>TACAAGTAATTTAACTTGGAAAAATGGCGTTGCATTTTAC<br>TCTAATAACGCTCAAGGCGACGGCAAAGATAAACTAAAG<br>GAACCTATTATAGAACATAGTACTCCTATCGAACTTGAAT<br>TTAAATCAGAGCCGCCAGTGGAGAAGCATGAATTGACTG<br>GTACAATCGAAGAAAGTAATGATTCTAAGCCAATTGATT<br>TTGAATATCATACAGCTGTTGAAGGTGCAGAAGGTCATG<br>CAGAAGGTACCATTGAAACTGAAGAAGATTCTATTCATG<br>TAGACTTTGAAGAATCGACACATGAAAATTCAAAACATC<br>ATGCTGATGTTGTTGAATATGAAGAAGATACAAACCCAG<br>GTGGTGGTCAGGTTACTACTGAGTCTAACCTAGTTGAATT<br>TGACGAAGATTCTACAAAAGGTATTGTAACTGGTGCTGT<br>TAGCGATCATACAACAATTGAAGATACGAAAGAATATAC<br>GACTGAAAGTAATCTGATTGAACTAGTAGATGAACTACC<br>TGAAGAACATGGTCAAGCGCAAGGACCAATCGAGGAAA<br>TTACTGAAAACAATCATCATATTTCTCATTCTGGTTTAGG<br>AACTGAAAATGGTCACGGTAATTATGGCGTGATTGAAGA<br>AATCGAAGAAAATAGCCACGTGGATATTAAGAGTGAATT<br>AGGTTACGAAGGTGGCCAAAATAGCGGTAATCAGTCATT<br>TGAGGAAGACACAGAAGAAGATAAACCGAAATATGAAC<br>AAGGTGGCAATATCGTAGATATCGATTTCGATAGTGTAC<br>CTCAAATTCATGGTCAAAATAATGGTAACCAATCATTCG<br>AAGAAGATACAGAGAAAGACAAACCTAAGTATGAACAA<br>GGTGGTAATATCATTGATATCGACTTCGACAGTGTGCCAC<br>ATATTCACGGATTCAATAAGCACACTGAAATTATTGAAG<br>AAGATACAAATAAAGATAAACCAAATTATCAATTCGGTG<br>GACACAATAGTGTTGACTTTGAAGAAGATACACTTCCAC<br>AAGTAAGTGGTCATAATGAAGGTCAACAAACGATTGAAG<br>AAGATACAACACCTCCAATCGTGCCACCAACGCCACCGA<br>CACCAGAAGTACCAAGCGAGCCGGAAACACCAACACCA<br>CCGACACCAGAAGTACCAAGCGAGCCGGAAACACCAAC<br>ACCGCCAACGCCAGAGGTACCAACTGAACCTGGTAAACC<br>AATACCACCTGCTAAAGAAGAACCTAAAAAACCTTCTAA<br>ACCAGTGGAACAAGGTAAAGTAGTAACACCTGTTATTGA<br>AATCAATGAAAAGGTTAAAGCAGTGGTACCAACTAAAAA<br>AGCACAATCTAAGAAATCTGAACTACCTGAAACAGGTGG<br>AGAAGAATCAACAAACAACGGCATGTTGTTCGGCGGATT<br>ATTTAGCATTTTAGGTTTAGCGTTATTACGCAGAAATAAA<br>AAGAATCACAAAGCATAA |
| 12 | Fibronectin-binding protein A (FnBPA) | MKNNLRYGIRKHKLGAASVFLGTMIVVGMGQDKEAAASE<br>QKTTTVEENGNSATDNKVNETQTTTTNVNTIDETQSYSATA<br>TEQPSNATQVTTEKAPKAVQAPQTAQPANVETVKEEVVKE<br>EANPQVKETTQSQDNSGDQRQVDLTPKKATQNQAAETQVE<br>VAQPRTVSESKPRVTRSADVAEAKEASDAKVETGTDVTSK<br>VTVESGSIEAPQGNKVEPHAGQRVVLKYKLKFEKGLHKGD<br>YFDFTLSNNVNTYGVSTARKVPEIKNGSVVMATGQLLGNG<br>KIRYTFTDYIDYKVNVTADLEINLFIDPKTVQSNGQQTITSTL<br>NDKETKNTLPIEYNPGVSNSYANVNGSIETFDKGNNKFTHV<br>AYIKPQNGHKSDSVSITGTLTQGSKANGNVPTVKVYEVLKD<br>AKELPESVYANISDSTMFKDVTQEMKDKLKVENNGSYKLD<br>IEKLEKSYVIHYDGEYLSGSDQVNFRTHMFGYPEQQYKYY<br>YTHLGYQLTWDNGLVLYSNKAKGDGTNGTITESNNMTFDE<br>EYGTGVITGQYDKNLVTTVEEEYDSSTLDIDYHTAIDGEGG<br>YVDGYIETIEETDSSAIDIDYHTAVDSEAGHVGGYTESSEES<br>NPIDFEESTHENSKHHADVVEYEEDTNPGGGQVTTESNLVE<br>FDEESTKGIVTGAVSDHTTIEDTKEYTTESNLIELVDELPEEH<br>GQAQGPIEEITENNHHISHSGLGTENGHGNYGVIEEIEENSH<br>VDIKSELGYEGGQNSGNQSFEEDTEEDKPKYEQGGNIVDID<br>FDSVPQIHGQNKGDQSFEEDTEKDKPKYEQGGNIIDIDFDSV<br>PQIFIGFNKHNEIIEEDTNKDKPNYQFGGHNIVDFEEDTLPKV<br>SGQNEGQQTIEEDTTPPTPPTPEVPSEPETPTPPTPEVPSEPET<br>PTPPTPEVPSEPETPTPPTPEVPSEPETPTPPTPEVPVEPGKPVP<br>PAKEEPKKPSKPVEQGKVVTPVIEINEKVKAVAPTKQKQSK<br>KSELPETGGEESTNKGMLFGGLFSILGLALLRRNKKNNKA |
| 13 | Fibronectin-binding protein B (FnBPB) | MKSNLRYGIRKHKLGAASVFLGTMIVVGMGQEKEAAASEQ<br>NNTTVEESGSSATESKASETQTTTNNVNTIDETQSYSATSTE<br>QPSQSTQVTTEEAPKTVQAPKVETSRVDLPSEKVADKETTG<br>TQVDIAQPSNVSEIKPRMKRSTDVTAVAEKEVVEETKATGT<br>DVTNKVEVEEGSEIVGHKQDTNVVNPHNAERVTLKYKWK<br>FGEGIKAGDYFDFTLSDNVETHGISTLRKVPEIKSTDGQVMA<br>TGEIIGERKVRYTFKEYVQEKKDLTAELSLNLFIDPTTVTQK<br>GNQNVEVKLGETTVSKIFNIQYLGGVRDNWGVTANGRIDT<br>LNKVDGKFSHFAYMKPNNQSLSSVTVTGQVTKGNKPGVN<br>NPTVKVYKHIGSDDLAESVYAKLDDVSKFEDVTDNMSLDF |

-continued

| SEQ ID NO: | Description | Sequence |
|---|---|---|
| | | DTNGGYSLNFNNLDQSKNYVIKYEGYYDSNASNLEFQTHL FGYYNYYYTSNLTWKNGVAFYSNNAQGDGKDKLKEPIIEH STPIELEFKSEPPVEKHELTGTIEESNDSKPIDFEYHTAVEGA EGHAEGTIETEEDSIHVDFEESTHENSKHHADVVEYEEDTNP GGGQVTTESNLVEFDEDSTKGIVTGAVSDHTTIEDTKEYTTE SNLIELVDELPEEHGQAQGPIEEITENNHHISHSGLGTENGHG NYGVIEEIEENSHVDIKSELGYEGGQNSGNQSFEEDTEEDKP KYEQGGNIVDIDFDSVPQIHGQNNGNQSFEEDTEKDKPKYE QGGNIIDIDFDSVPHIHGFNKHTEIIEEDTNKDKPNYQFGGH NSVDFEEDTLPQVSGHNEGQQTIEEDTTPPIVPPTPPTPEVPS EPETPTPPTPEVPSEPETPTPPTPEVPTEPGKPIPPAKEEPKKPS KPVEQGKVVTPVIEINEKVKAVVPTKKAQSKKSELPETGGE ESTNNGMLFGGLFSILGLALLRRNKKNHKA |

The invention claimed is:

1. A method of treating a gastrointestinal cancer in a subject in need thereof, wherein the method comprises administering a pharmaceutically effective amount of a recombinant, probiotic lactic acid bacterium into the gastrointestinal tract of the subject, wherein the bacterium comprises a non-replicating plasmid vector comprising (a) a tumor suppressor gene operably linked to a first promoter that directs expression of the tumor suppressor gene in a mammalian cell, wherein the first promoter is a mammalian promoter, and wherein the tumor suppressor gene is DUSP10, and (b) an adhesin gene operably linked to a second promoter that directs expression of the adhesin gene in the bacterium, wherein the second promoter is a prokaryotic promoter, and wherein the adhesin is fibronectin-binding protein.

2. The method of claim 1, wherein the bacterium is a lactic-acid producing bacterium.

3. The method of claim 2, wherein the bacterium is of the *Lactococcus* genus.

4. The method of claim 3, wherein the bacterium is *Lactococcus lactis*.

5. The method of claim 1, wherein the method further comprises administering a pharmaceutically effective amount of immune checkpoint inhibitor, optionally wherein the immune checkpoint inhibitor is anti-programmed death ligand-1 (PDL-1).

6. The method of claim 1, wherein the cancer is selected from the group consisting of esophageal cancer, gastric cancer, colorectal cancer and anal cancer.

7. The method of claim 6, wherein the cancer is colorectal cancer.

8. The method of claim 1, wherein the method reduces inflammation of the esophagus, the stomach, the small intestine, the caecum, the large intestine, or the anus.

9. The method of claim 1, wherein the recombinant, probiotic lactic acid bacterium is administered orally.

10. The method of claim 1, wherein the subject is a human.

* * * * *

SEQUENCE LISTING

<160> NUMBER OF SEQ ID NOS: 13

<210> SEQ ID NO 1
<211> LENGTH: 1449
<212> TYPE: DNA
<213> ORGANISM: Artificial Sequence
<220> FEATURE:
<223> OTHER INFORMATION: DUSP10

<400> SEQUENCE: 1

```
atgcctccgt ctcctttaga cgacagggta gtagtggcac tatctaggcc cgtccgacct     60

caggatctca acctttgttt agactctagt taccttggct ctgccaaccc aggcagtaac    120

agccaccctc ctgtcatcgc caccaccgtt gtgtccctca aggctgcgaa tctgacgtat    180

atgccctcat ccagcggctc tgcccgctcg ctgaattgtg gatgcagcag tgccagctgc    240

tgcactgtgg caacctacga caaggacaat caggcccaaa cccaagccat tgccgctggc    300

accaccacca ctgccatcgg aacctctacc acctgccctg ctaaccagat ggtcaacaat    360

aatgagaata caggctctct aagtccatca agtggggtgg gcagccctgt gtcagggacc    420

cccaagcagc tagccagcat caaaataatc taccccaatg acttggcaaa gaagatgacc    480

aaatgcagca agagtcacct gccgagtcag ggccctgtca tcattgactg caggcccttc    540

atggagtaca acaagagtca catccaagga gctgtccaca ttaactgtgc cgataagatc    600

agccggcgga gactgcagca gggcaagatc actgtcctag acttgatttc ctgtagggaa    660

ggcaaggact ctttcaagag gatcttttcc aaagaaatta tagtttatga tgagaatacc    720

aatgaaccaa gccgagtgat gccctcccag ccacttcaca tagtcctcga gtccctgaag    780

agagaaggca aagaacctct ggtgttgaaa ggtggactta gtagttttaa gcagaaccat    840

gaaaacctct gtgacaactc cctccagctc caagagtgcc gggaggtggg gggcggcgca    900

tccgcggcct cgagcttgct acctcagccc atccccacca cccctgacat cgagaacgct    960

gagctcaccc ccatcttgcc cttcctgttc cttggcaatg agcaggatgc tcaggacctg   1020

gacaccatgc agcggctgaa catcggctac gtcatcaacg tcaccactca tcttcccctc   1080

taccactatg agaaaggcct gttcaactac aagcggctgc cagccactga cagcaacaag   1140

cagaacctgc ggcagtactt tgaagaggct tttgagttca ttgaggaagc tcaccagtgt   1200

gggaaggggc ttctcatcca ctgccaggct ggggtgtccc gctccgccac catcgtcatc   1260

gcttacttga tgaagcacac tcggatgacc atgactgatg cttataaatt tgtcaaaggc   1320

aaacgaccaa ttatctcccc aaaccttaac ttcatggggc agttgctaga gttcgaggaa   1380
```

gacctaaaca acggtgtgac accgagaatc cttacaccaa agctgatggg cgtggagacg 1440
gttgtgtga 1449

<210> SEQ ID NO 2
<211> LENGTH: 129
<212> TYPE: DNA
<213> ORGANISM: Artificial Sequence
<220> FEATURE:
<223> OTHER INFORMATION: PH promoter

<400> SEQUENCE: 2
atcatggaga taattaaaat gataaccatc tcgcaaataa ataagtattt tactgttttc 60
gtaacagttt tgtaataaaa aaacctataa atattccgga ttattcatac cgtcccacca 120
tcgggcgcg 129

<210> SEQ ID NO 3
<211> LENGTH: 576
<212> TYPE: DNA
<213> ORGANISM: Artificial Sequence
<220> FEATURE:
<223> OTHER INFORMATION: CMV promoter

<400> SEQUENCE: 3
tagtaatcaa ttacggggtc attagttcat agcccatata tggagttccg cgttacataa 60
cttacggtaa atggcccgcc tggctgaccg cccaacgacc cccgcccatt gacgtcaata 120
atgacgtatg ttcccatagt aacgccaata gggactttcc attgacgtca atgggtggag 180
tatttacggt aaactgccca cttggcagta catcaagtgt atcatatgcc aagtacgccc 240
cctattgacg tcaatgacgg taaatggccc gcctggcatt atgcccagta catgacctta 300
tgggactttc ctacttggca gtacatctac gtattagtca tcgctattac catggtgatg 360
cggttttggc agtacatcaa tgggcgtgga tagcggtttg actcacgggg atttccaagt 420
ctccacccca ttgacgtcaa tgggagtttg ttttggcacc aaaatcaacg ggactttcca 480
aaatgtcgta acaactccgc cccattgacg caaatgggcg gtaggcgtgt acggtgggag 540
gtctatataa gcagagctgg tttagtgaac cgtcag 576

<210> SEQ ID NO 4
<211> LENGTH: 345
<212> TYPE: DNA
<213> ORGANISM: Artificial Sequence
<220> FEATURE:
<223> OTHER INFORMATION: SV40 promoter

<400> SEQUENCE: 4
ctgtggaatg tgtgtcagtt agggtgtgga aagtccccag gctccccagc aggcagaagt 60
atgcaaagca tgcatctcaa ttagtcagca accaggtgtg gaaagtcccc aggctcccca 120
gcaggcagaa gtatgcaaag catgcatctc aattagtcag caaccatagt cccgccccta 180
actccgccca tcccgcccct aactccgccc agttccgccc attctccgcc ccatggctga 240
ctaatttttt ttatttatgc agaggccgag gccgcctctg cctctgagct attccagaag 300
tagtgaggag gcttttttgg aggcctaggc ttttgcaaaa agctc 345

<210> SEQ ID NO 5
<211> LENGTH: 753
<212> TYPE: DNA
<213> ORGANISM: Artificial Sequence
<220> FEATURE:

<223> OTHER INFORMATION: TK promoter

<400> SEQUENCE: 5

```
aaatgagtct tcggacctcg cgggggccgc ttaagcggtg gttagggttt gtctgacgcg     60
gggggagggg gaaggaacga aacactctca ttcggaggcg gctcggggtt tggtcttggt    120
ggccacgggc acgcagaaga gcgccgcgat cctcttaagc acccccccgc cctccgtgga    180
ggcgggggtt tggtcggcgg gtggtaactg gcgggccgct gactcgggcg ggtcgcgcgc    240
cccagagtgt gaccttttcg gtctgctcgc agacccccgg gcggcgccgc cgcggcggcg    300
acgggctcgc tgggtcctag gctccatggg gaccgtatac gtggacaggc tctggagcat    360
ccgcacgact gcggtgatat taccggagac cttctgcggg acgagccggg tcacgcggct    420
gacgcggagc gtccgttggg cgacaaacac caggacgggg cacaggtaca ctatcttgtc    480
acccggaggc gcgagggact gcaggagctt cagggagtgg cgcagctgct tcatccccgt    540
ggcccgttgc tcgcgtttgc tggcggtgtc cccggaagaa atatatttgc atgtctttag    600
ttctatgatg acacaaaccc cgcccagcgt cttgtcattg gcgaattcga acacgcagat    660
gcagtcgggg cggcgcggtc ccaggtccac ttcgcatatt aaggtgacgc gtgtggcctc    720
gaacaccgag cgaccctgca gcgacccgct taa                                 753
```

<210> SEQ ID NO 6
<211> LENGTH: 633
<212> TYPE: DNA
<213> ORGANISM: Artificial Sequence
<220> FEATURE:
<223> OTHER INFORMATION: LTR promoter

<400> SEQUENCE: 6

```
tggaagggct aattcactcc caacgaagac aagatatcct tgatctgtgg atctaccaca     60
cacaaggcta cttccctgat tagcagaact acacaccagg gccagggatc agatatccac    120
tgacctttgg atggtgctac aagctagtac cagttgagcc agagaagtta gaagaagcca    180
acaaaggaga gaacaccagc ttgttacacc ctgtgagcct gcatggaatg gatgacccgg    240
agagagaagt gttagagtgg aggtttgaca gccgcctagc atttcatcac atggcccgag    300
agctgcatcc ggagtacttc aagaactgct gacatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agc                                 633
```

<210> SEQ ID NO 7
<211> LENGTH: 3280
<212> TYPE: DNA
<213> ORGANISM: Artificial Sequence
<220> FEATURE:
<223> OTHER INFORMATION: Fibronectin binding protein A

<400> SEQUENCE: 7

```
gcatttaaag ggagatatta tagtgaaaaa caatcttagg tacggcatta gaaaacataa     60
attgggagca gcatcagtat tcttaggaac aatgatcgtt gttgggatgg gacaagataa    120
agaagctgca gcatcagaac aaaagacaac tacagtagaa gaaaatggga attcagctac    180
tgataataaa gtaaacgaaa cacaaacaac tacaactaac gttaatacta tagatgaaac    240
```

```
acaatcatac agcgcaacag caacagaaca accgtcaaac gcaacacaag taacaactga    300
aaaagcacca aaagcagtac aagcaccaca aactgcacaa ccagcaaatg tagaaacagt    360
taaagaagag gtagttaagg aagaagcgaa ccctcaagtt aaggaaacga cacaatctca    420
agacaatagc ggagatcaaa gacaagtaga tttaacacct aaaaaggcta cacaaaatca    480
agcagcagaa acacaagttg aagtggcaca gccaagaacg gtatcagaaa gtaaaccacg    540
tgtgacaaga tcagcagatg tagcggaagc taaggaagct agtgacgcga aagtggaaac    600
gggtacagat gtgacaagta aagttacagt ggaaagtggt tctattgagg cacctcaagg    660
aaataaagta gagccacatg ctggtcaacg tgtcgtactg aaatacaaat tgaaattcga    720
aaagggttta cacaaaggag attattttga tttcaccttg tctaataatg taaatactta    780
tggagtttca acagctagaa aagtaccaga aatcaaaaat ggttcagtcg taatggcgac    840
aggtcaactt cttggaaatg ggaaaattag gtatacattt acagactata ttgattataa    900
agtaaatgtg actgctgatt tagaaatcaa tttatttatt gatcctaaaa ctgtacaaag    960
caatggacaa caaacaataa cttcaacgtt gaatgataag gaaacaaaaa acacattgcc   1020
aatagaatat aatccaggag taagtaatag ctatgctaat gtaaatggat ctattgaaac   1080
ttttgataaa gggaacaata aattcactca tgtagcttac ataaaaccac aaaatgggca   1140
taaatcagat agcgtttcaa ttactggtac actaactcaa ggtagcaaag ctaatggaaa   1200
tgttccaact gtaaaagtat atgaagtctt aaaggatgct aaagaattac cagaaagtgt   1260
atatgcaaac atatcagact ctacaatgtt taaagatgta actcaggaaa tgaaagataa   1320
attaaaagta gaaaataatg ggagttataa attagacatt gagaaattag aaaaaagtta   1380
tgttatacac tatgatggtg aatacttaag tggttcagat caagtgaatt ttagaacgca   1440
tatgtttgga tatccagaac agcagtataa gtactactat actcatttgg gataccaact   1500
tacatgggat aatggattag ttttatatag taacaaagca aaaggtgatg gaacgaatgg   1560
aacaataaca gaatcgaata atatgacatt tgatgaagaa tatggaactg gagttattac   1620
aggtcaatat gataagaatt tagtaactac tgttgaagaa gaatatgatt cttcaactct   1680
tgacattgat taccacacag ctatagatgg tgaaggtggt tatgttgatg gatacattga   1740
aacaatagaa gaaacggatt catcagctat tgatatcgat taccatactg ctgtggatag   1800
cgaagcgggt cacgttggag gatacactga gtcctctgag gaatcaaatc caattgactt   1860
tgaagaatct acgcatgaaa attcaaaaca tcacgctgat gttgttgaat atgaagagga   1920
tacaaaccca ggtggtggtc aggttactac tgagtctaac ttagttgaat ttgacgaaga   1980
gtctacaaaa ggtattgtaa ctggcgcagt gagcgaccat acaacaattg aagatacgaa   2040
agaatataca actgaaagta atctgattga actagtagat gaactacctg aagaacatgg   2100
tcaagcacaa ggaccaatcg aggaaattac tgaaaacaat catcatattt ctcattctgg   2160
tttaggaact gaaaatggtc acggtaatta tggtgtgatt gaagaaatcg aagaaaatag   2220
ccatgttgat attaagagtg aattaggtta tgaaggtggc caaaatagcg gtaaccagtc   2280
attcgaggaa gacacagaag aagataaacc taaatatgaa caaggtggca atatcgtaga   2340
tatcgatttc gatagtgtac ctcaaattca tggtcaaaat aaaggtgatc agtcattcga   2400
agaagataca gagaaagaca aacctaagta tgaacaaggt ggtaatatca ttgatatcga   2460
cttcgacagt gtgccacaaa ttcatggatt caataagcat aatgaaatta ttgaagaaga   2520
tacaaacaaa gataaaccaa attatcaatt cggtggacac aacattgttg attttgaaga   2580
```

```
agatacactt ccgaaagtaa gcggtcaaaa tgaaggtcaa caaacgattg aagaagatac   2640

aacgccgcca acgccaccga caccagaagt accgagtgag ccggaaacac caacaccacc   2700

gacgccggaa gtaccgagtg agccagaaac accaacgcca ccgacaccag aagtaccaag   2760

tgagccggaa acaccaacac cgccaacacc agaggtacca agtgagccgg aaacaccaac   2820

accgccaaca ccagaggtac cagttgaacc tggtaaacca gtaccacctg ctaaagaaga   2880

acctaaaaaa ccttctaaac cagtggaaca aggtaaagta gtaacacctg ttattgaaat   2940

caatgaaaag gttaaagcag tggcaccaac taaacaaaaa caatctaaga aatctgaact   3000

acctgaaaca ggtggagaag aatcaacaaa caaaggtatg ttgttcggcg gattattcag   3060

cattctaggt ttagcgttat tacgtagaaa taaaaagaat aacaaagcat aattaacaaa   3120

aattgacggg tttatttcat aaattacatg aagtaagcct gttttttta tattaaatca   3180

aatttttaat agaaaattag agtgttttct gattgcttca ttggtttatg tctgatgatt   3240

gataacgaac tgagagataa agttagaatt ttaaactagt                         3280
```

<210> SEQ ID NO 8
<211> LENGTH: 559
<212> TYPE: DNA
<213> ORGANISM: Artificial Sequence
<220> FEATURE:
<223> OTHER INFORMATION: erm promoter

<400> SEQUENCE: 8

```
cggtatcgat aagcttagtc tagaatcgat acgattttga agtggcaaca gataaaaaaa     60

agcagtttaa aattgttgct gaacttttaa aacaagcaaa tacaatcatt gtcgcaacag    120

atagcgacag agaaggcgaa aacattgcct ggtcgatcat tcataaagca aatgcctttt    180

ctaaagataa aacgtataaa agactatgga tcaatagttt agaaaaagat gtgatccgta    240

gcggttttca aaatttgcaa ccaggaatga attactatcc cttttatcaa gaagcgcaca    300

aaaagaaaaa cgaaatgata caccaatcag tgcaaaaaaa gatataatgg gagataagac    360

ggttcgtgtt cgtgctgact tgcaccatat cataaaaatc gaaacagcaa agaatggcgg    420

aaacgtaaaa gaagttatgg aaataagact tagaagcaaa cttaagagtg tgttgatagt    480

gcagtatctt aaaattttgt ataataggaa ttgaagttaa attagatgct aaaaatttgt    540

aattaagaag gagtgaatt                                                 559
```

<210> SEQ ID NO 9
<211> LENGTH: 309
<212> TYPE: DNA
<213> ORGANISM: Artificial Sequence
<220> FEATURE:
<223> OTHER INFORMATION: nisin promoter

<400> SEQUENCE: 9

```
ctcctgtttt acaaccgggt gtacatagcg aaatacttgt aatgcgtggt gatgcacctg     60

aatctttctt cgaaacagat accaaatcca agctaaaatc ttttgtactc attttgagtg    120

cctccttata atttattttg tagttccttc gaacgaaatc attgtatcta acaaacttca    180

gaatttaatc agagccgttt attatgctcg cgttatcgac aataatatta ttaccaatac    240

tttctcaaga tagaattaag actgttttag atttgttaat gtttctattg tcagtatagt    300

tataagact                                                            309
```

<210> SEQ ID NO 10
<211> LENGTH: 482

<212> TYPE: PRT
<213> ORGANISM: Artificial Sequence
<220> FEATURE:
<223> OTHER INFORMATION: DUSP10

<400> SEQUENCE: 10

```
Met Pro Pro Ser Pro Leu Asp Asp Arg Val Val Val Ala Leu Ser Arg
1               5                   10                  15

Pro Val Arg Pro Gln Asp Leu Asn Leu Cys Leu Asp Ser Ser Tyr Leu
            20                  25                  30

Gly Ser Ala Asn Pro Gly Ser Asn Ser His Pro Pro Val Ile Ala Thr
        35                  40                  45

Thr Val Val Ser Leu Lys Ala Ala Asn Leu Thr Tyr Met Pro Ser Ser
    50                  55                  60

Ser Gly Ser Ala Arg Ser Leu Asn Cys Gly Cys Ser Ser Ala Ser Cys
65                  70                  75                  80

Cys Thr Val Ala Thr Tyr Asp Lys Asp Asn Gln Ala Gln Thr Gln Ala
                85                  90                  95

Ile Ala Ala Gly Thr Thr Thr Thr Ala Ile Gly Thr Ser Thr Thr Cys
            100                 105                 110

Pro Ala Asn Gln Met Val Asn Asn Asn Glu Asn Thr Gly Ser Leu Ser
        115                 120                 125

Pro Ser Ser Gly Val Gly Ser Pro Val Ser Gly Thr Pro Lys Gln Leu
    130                 135                 140

Ala Ser Ile Lys Ile Ile Tyr Pro Asn Asp Leu Ala Lys Lys Met Thr
145                 150                 155                 160

Lys Cys Ser Lys Ser His Leu Pro Ser Gln Gly Pro Val Ile Ile Asp
                165                 170                 175

Cys Arg Pro Phe Met Glu Tyr Asn Lys Ser His Ile Gln Gly Ala Val
            180                 185                 190

His Ile Asn Cys Ala Asp Lys Ile Ser Arg Arg Arg Leu Gln Gln Gly
        195                 200                 205

Lys Ile Thr Val Leu Asp Leu Ile Ser Cys Arg Glu Gly Lys Asp Ser
    210                 215                 220

Phe Lys Arg Ile Phe Ser Lys Glu Ile Ile Val Tyr Asp Glu Asn Thr
225                 230                 235                 240

Asn Glu Pro Ser Arg Val Met Pro Ser Gln Pro Leu His Ile Val Leu
                245                 250                 255

Glu Ser Leu Lys Arg Glu Gly Lys Glu Pro Leu Val Leu Lys Gly Gly
            260                 265                 270

Leu Ser Ser Phe Lys Gln Asn His Glu Asn Leu Cys Asp Asn Ser Leu
        275                 280                 285

Gln Leu Gln Glu Cys Arg Glu Val Gly Gly Gly Ala Ser Ala Ala Ser
    290                 295                 300

Ser Leu Leu Pro Gln Pro Ile Pro Thr Thr Pro Asp Ile Glu Asn Ala
305                 310                 315                 320

Glu Leu Thr Pro Ile Leu Pro Phe Leu Phe Leu Gly Asn Glu Gln Asp
                325                 330                 335

Ala Gln Asp Leu Asp Thr Met Gln Arg Leu Asn Ile Gly Tyr Val Ile
            340                 345                 350

Asn Val Thr Thr His Leu Pro Leu Tyr His Tyr Glu Lys Gly Leu Phe
        355                 360                 365

Asn Tyr Lys Arg Leu Pro Ala Thr Asp Ser Asn Lys Gln Asn Leu Arg
    370                 375                 380
```

```
Gln Tyr Phe Glu Glu Ala Phe Glu Phe Ile Glu Glu Ala His Gln Cys
385                 390                 395                 400

Gly Lys Gly Leu Leu Ile His Cys Gln Ala Gly Val Ser Arg Ser Ala
                405                 410                 415

Thr Ile Val Ile Ala Tyr Leu Met Lys His Thr Arg Met Thr Met Thr
            420                 425                 430

Asp Ala Tyr Lys Phe Val Lys Gly Lys Arg Pro Ile Ile Ser Pro Asn
        435                 440                 445

Leu Asn Phe Met Gly Gln Leu Leu Glu Phe Glu Glu Asp Leu Asn Asn
    450                 455                 460

Gly Val Thr Pro Arg Ile Leu Thr Pro Lys Leu Met Gly Val Glu Thr
465                 470                 475                 480

Val Val
```

<210> SEQ ID NO 11
<211> LENGTH: 2823
<212> TYPE: DNA
<213> ORGANISM: Artificial Sequence
<220> FEATURE:
<223> OTHER INFORMATION: Fibronectin binding protein B

<400> SEQUENCE: 11

```
gtgaaaagca atcttagata cggcataaga aaacacaaat tgggagcggc ctcagtattc     60

ttaggaacaa tgatcgttgt tggaatggga caagaaaaag aagctgcagc atcggaacaa    120

aacaatacta cagtagagga aagtgggagt tcagctactg aaagtaaagc aagcgaaaca    180

caaacaacta caaataacgt taatacaata gatgaaacac aatcatacag cgcgacatca    240

actgagcaac catcacaatc aacacaagta acaacagaag aagcaccgaa aactgtgcaa    300

gcaccaaaag tagaaacttc gcgagttgat ttgccatcgg aaaaagttgc tgataaggaa    360

actacaggaa ctcaagttga catagctcaa ccaagtaacg tctcagaaat taaaccaaga    420

atgaaaagat caactgacgt tacagcagtt gcagagaaag aagtagtgga agaaactaaa    480

gcgacaggta cagatgtaac aaataaagtg gaagtagaag aaggtagtga aattgtagga    540

cataaacaag atacgaatgt tgtaaatcct cataacgcag aaagagtaac cttgaaatat    600

aaatggaaat ttggagaagg aattaaggcg ggagattatt ttgatttcac attaagcgat    660

aatgttgaaa ctcatggtat ctcaacactg cgtaaagttc cggagataaa aagtacagat    720

ggtcaagtta tggcgacagg agaaataatt ggagaaagaa aagttagata tacgtttaaa    780

gaatatgtac aagaaaagaa agatttaact gctgaattat ctttaaatct atttattgat    840

cctacaacag tgacgcaaaa aggtaaccaa aatgttgaag ttaaattggg tgagactacg    900

gttagcaaaa tatttaatat tcaatattta ggtggagtta gagataattg ggggagtaaca    960

gctaatggtc gaattgatac tttaaataaa gtagatggga aatttagtca ttttgcgtac   1020

atgaaaccta acaaccagtc gttaagctct gtgacagtaa ctggtcaagt aactaaagga   1080

aataaaccag ggttaataa tccaacagtt aaggtatata aacacattgg ttcagacgat   1140

ttagctgaaa gcgtatatgc aaagcttgat gatgtcagca aatttgaaga tgtgactgat   1200

aatatgagtt tagattttga tactaatggt ggttattctt taaactttaa taatttagac   1260

caaagtaaaa attatgtaat aaaatatgaa gggtattatg attcaaatgc tagcaactta   1320

gaatttcaaa cacacctttt tggatattat aactattatt atacaagtaa tttaacttgg   1380

aaaaatggcg ttgcatttta ctctaataac gctcaaggcg acggcaaaga taaactaaag   1440

gaacctatta tagaacatag tactcctatc gaacttgaat ttaaatcaga gccgccagtg   1500
```

```
gagaagcatg aattgactgg tacaatcgaa gaaagtaatg attctaagcc aattgatttt   1560

gaatatcata cagctgttga aggtgcagaa ggtcatgcag aaggtaccat tgaaactgaa   1620

gaagattcta ttcatgtaga ctttgaagaa tcgacacatg aaaattcaaa acatcatgct   1680

gatgttgttg aatatgaaga agatacaaac ccaggtggtg gtcaggttac tactgagtct   1740

aacctagttg aatttgacga agattctaca aaaggtattg taactggtgc tgttagcgat   1800

catacaacaa ttgaagatac gaaagaatat acgactgaaa gtaatctgat tgaactagta   1860

gatgaactac ctgaagaaca tggtcaagcg caaggaccaa tcgaggaaat tactgaaaac   1920

aatcatcata tttctcattc tggtttagga actgaaaatg gtcacggtaa ttatggcgtg   1980

attgaagaaa tcgaagaaaa tagccacgtg gatattaaga gtgaattagg ttacgaaggt   2040

ggccaaaata gcggtaatca gtcatttgag gaagacacag aagaagataa accgaaatat   2100

gaacaaggtg gcaatatcgt agatatcgat ttcgatagtg tacctcaaat tcatggtcaa   2160

aataatggta accaatcatt cgaagaagat acagagaaag acaaacctaa gtatgaacaa   2220

ggtggtaata tcattgatat cgacttcgac agtgtgccac atattcacgg attcaataag   2280

cacactgaaa ttattgaaga agatacaaat aaagataaac caaattatca attcggtgga   2340

cacaatagtg ttgactttga agaagataca cttccacaag taagtggtca taatgaaggt   2400

caacaaacga ttgaagaaga tacaacacct ccaatcgtgc caccaacgcc accgacacca   2460

gaagtaccaa gcgagccgga aacaccaaca ccaccgacac cagaagtacc aagcgagccg   2520

gaaacaccaa caccgccaac gccagaggta ccaactgaac ctggtaaacc aataccacct   2580

gctaaagaag aacctaaaaa accttctaaa ccagtggaac aaggtaaagt agtaacacct   2640

gttattgaaa tcaatgaaaa ggttaaagca gtggtaccaa ctaaaaaagc acaatctaag   2700

aaatctgaac tacctgaaac aggtggagaa gaatcaacaa acaacggcat gttgttcggc   2760

ggattattta gcattttagg tttagcgtta ttacgcagaa ataaaaagaa tcacaaagca   2820

taa                                                                 2823
```

<210> SEQ ID NO 12
<211> LENGTH: 1029
<212> TYPE: PRT
<213> ORGANISM: Artificial Sequence
<220> FEATURE:
<223> OTHER INFORMATION: Fibronectin binding protein A

<400> SEQUENCE: 12

```
Met Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
            20                  25                  30

Lys Glu Ala Ala Ala Ser Glu Gln Lys Thr Thr Thr Val Glu Glu Asn
        35                  40                  45

Gly Asn Ser Ala Thr Asp Asn Lys Val Asn Glu Thr Gln Thr Thr Thr
    50                  55                  60

Thr Asn Val Asn Thr Ile Asp Glu Thr Gln Ser Tyr Ser Ala Thr Ala
65                  70                  75                  80

Thr Glu Gln Pro Ser Asn Ala Thr Gln Val Thr Thr Glu Lys Ala Pro
                85                  90                  95

Lys Ala Val Gln Ala Pro Gln Thr Ala Gln Pro Ala Asn Val Glu Thr
            100                 105                 110

Val Lys Glu Glu Val Val Lys Glu Glu Ala Asn Pro Gln Val Lys Glu
```

```
        115                 120                 125

Thr Thr Gln Ser Gln Asp Asn Ser Gly Asp Gln Arg Gln Val Asp Leu
    130                 135                 140

Thr Pro Lys Lys Ala Thr Gln Asn Gln Ala Ala Glu Thr Gln Val Glu
145                 150                 155                 160

Val Ala Gln Pro Arg Thr Val Ser Glu Ser Lys Pro Arg Val Thr Arg
                165                 170                 175

Ser Ala Asp Val Ala Glu Ala Lys Glu Ala Ser Asp Ala Lys Val Glu
            180                 185                 190

Thr Gly Thr Asp Val Thr Ser Lys Val Thr Val Glu Ser Gly Ser Ile
        195                 200                 205

Glu Ala Pro Gln Gly Asn Lys Val Glu Pro His Ala Gly Gln Arg Val
    210                 215                 220

Val Leu Lys Tyr Lys Leu Lys Phe Glu Lys Gly Leu His Lys Gly Asp
225                 230                 235                 240

Tyr Phe Asp Phe Thr Leu Ser Asn Asn Val Asn Thr Tyr Gly Val Ser
                245                 250                 255

Thr Ala Arg Lys Val Pro Glu Ile Lys Asn Gly Ser Val Val Met Ala
            260                 265                 270

Thr Gly Gln Leu Leu Gly Asn Gly Lys Ile Arg Tyr Thr Phe Thr Asp
        275                 280                 285

Tyr Ile Asp Tyr Lys Val Asn Val Thr Ala Asp Leu Glu Ile Asn Leu
    290                 295                 300

Phe Ile Asp Pro Lys Thr Val Gln Ser Asn Gly Gln Gln Thr Ile Thr
305                 310                 315                 320

Ser Thr Leu Asn Asp Lys Glu Thr Lys Asn Thr Leu Pro Ile Glu Tyr
                325                 330                 335

Asn Pro Gly Val Ser Asn Ser Tyr Ala Asn Val Asn Gly Ser Ile Glu
            340                 345                 350

Thr Phe Asp Lys Gly Asn Asn Lys Phe Thr His Val Ala Tyr Ile Lys
        355                 360                 365

Pro Gln Asn Gly His Lys Ser Asp Ser Val Ser Ile Thr Gly Thr Leu
    370                 375                 380

Thr Gln Gly Ser Lys Ala Asn Gly Asn Val Pro Thr Val Lys Val Tyr
385                 390                 395                 400

Glu Val Leu Lys Asp Ala Lys Glu Leu Pro Glu Ser Val Tyr Ala Asn
                405                 410                 415

Ile Ser Asp Ser Thr Met Phe Lys Asp Val Thr Gln Glu Met Lys Asp
            420                 425                 430

Lys Leu Lys Val Glu Asn Asn Gly Ser Tyr Lys Leu Asp Ile Glu Lys
        435                 440                 445

Leu Glu Lys Ser Tyr Val Ile His Tyr Asp Gly Glu Tyr Leu Ser Gly
    450                 455                 460

Ser Asp Gln Val Asn Phe Arg Thr His Met Phe Gly Tyr Pro Glu Gln
465                 470                 475                 480

Gln Tyr Lys Tyr Tyr Tyr Thr His Leu Gly Tyr Gln Leu Thr Trp Asp
                485                 490                 495

Asn Gly Leu Val Leu Tyr Ser Asn Lys Ala Lys Gly Asp Gly Thr Asn
            500                 505                 510

Gly Thr Ile Thr Glu Ser Asn Asn Met Thr Phe Asp Glu Glu Tyr Gly
        515                 520                 525

Thr Gly Val Ile Thr Gly Gln Tyr Asp Lys Asn Leu Val Thr Thr Val
    530                 535                 540
```

```
Glu Glu Glu Tyr Asp Ser Ser Thr Leu Asp Ile Asp Tyr His Thr Ala
545                 550                 555                 560

Ile Asp Gly Glu Gly Gly Tyr Val Asp Gly Tyr Ile Glu Thr Ile Glu
                565                 570                 575

Glu Thr Asp Ser Ser Ala Ile Asp Ile Asp Tyr His Thr Ala Val Asp
            580                 585                 590

Ser Glu Ala Gly His Val Gly Gly Tyr Thr Glu Ser Ser Glu Glu Ser
        595                 600                 605

Asn Pro Ile Asp Phe Glu Glu Ser Thr His Glu Asn Ser Lys His His
    610                 615                 620

Ala Asp Val Val Glu Tyr Glu Glu Asp Thr Asn Pro Gly Gly Gly Gln
625                 630                 635                 640

Val Thr Thr Glu Ser Asn Leu Val Glu Phe Asp Glu Glu Ser Thr Lys
                645                 650                 655

Gly Ile Val Thr Gly Ala Val Ser Asp His Thr Thr Ile Glu Asp Thr
            660                 665                 670

Lys Glu Tyr Thr Thr Glu Ser Asn Leu Ile Glu Leu Val Asp Glu Leu
        675                 680                 685

Pro Glu Glu His Gly Gln Ala Gln Gly Pro Ile Glu Glu Ile Thr Glu
    690                 695                 700

Asn Asn His His Ile Ser His Ser Gly Leu Gly Thr Glu Asn Gly His
705                 710                 715                 720

Gly Asn Tyr Gly Val Ile Glu Glu Ile Glu Glu Asn Ser His Val Asp
                725                 730                 735

Ile Lys Ser Glu Leu Gly Tyr Glu Gly Gly Gln Asn Ser Gly Asn Gln
            740                 745                 750

Ser Phe Glu Glu Asp Thr Glu Glu Asp Lys Pro Lys Tyr Glu Gln Gly
        755                 760                 765

Gly Asn Ile Val Asp Ile Asp Phe Asp Ser Val Pro Gln Ile His Gly
    770                 775                 780

Gln Asn Lys Gly Asp Gln Ser Phe Glu Glu Asp Thr Glu Lys Asp Lys
785                 790                 795                 800

Pro Lys Tyr Glu Gln Gly Gly Asn Ile Ile Asp Ile Asp Phe Asp Ser
                805                 810                 815

Val Pro Gln Ile His Gly Phe Asn Lys His Asn Glu Ile Ile Glu Glu
            820                 825                 830

Asp Thr Asn Lys Asp Lys Pro Asn Tyr Gln Phe Gly Gly His Asn Ile
        835                 840                 845

Val Asp Phe Glu Glu Asp Thr Leu Pro Lys Val Ser Gly Gln Asn Glu
    850                 855                 860

Gly Gln Gln Thr Ile Glu Glu Asp Thr Thr Pro Pro Thr Pro Pro Thr
865                 870                 875                 880

Pro Glu Val Pro Ser Glu Pro Glu Thr Pro Thr Pro Pro Thr Pro Glu
                885                 890                 895

Val Pro Ser Glu Pro Glu Thr Pro Thr Pro Pro Thr Pro Glu Val Pro
            900                 905                 910

Ser Glu Pro Glu Thr Pro Thr Pro Pro Thr Pro Glu Val Pro Ser Glu
        915                 920                 925

Pro Glu Thr Pro Thr Pro Pro Thr Pro Glu Val Pro Val Glu Pro Gly
    930                 935                 940

Lys Pro Val Pro Pro Ala Lys Glu Glu Pro Lys Lys Pro Ser Lys Pro
945                 950                 955                 960
```

```
Val Glu Gln Gly Lys Val Val Thr Pro Val Ile Glu Ile Asn Glu Lys
                965                 970                 975

Val Lys Ala Val Ala Pro Thr Lys Gln Lys Gln Ser Lys Lys Ser Glu
            980                 985                 990

Leu Pro Glu Thr Gly Gly Glu Glu  Ser Thr Asn Lys Gly  Met Leu Phe
        995                 1000                 1005

Gly Gly  Leu Phe Ser Ile Leu  Gly Leu Ala Leu Leu  Arg Arg Asn
    1010                 1015                 1020

Lys Lys  Asn Asn Lys Ala
    1025


<210> SEQ ID NO 13
<211> LENGTH: 940
<212> TYPE: PRT
<213> ORGANISM: Artificial Sequence
<220> FEATURE:
<223> OTHER INFORMATION: Fibronectin binding protein B

<400> SEQUENCE: 13

Met Lys Ser Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Glu
            20                  25                  30

Lys Glu Ala Ala Ala Ser Glu Gln Asn Asn Thr Thr Val Glu Glu Ser
        35                  40                  45

Gly Ser Ser Ala Thr Glu Ser Lys Ala Ser Glu Thr Gln Thr Thr Thr
    50                  55                  60

Asn Asn Val Asn Thr Ile Asp Glu Thr Gln Ser Tyr Ser Ala Thr Ser
65                  70                  75                  80

Thr Glu Gln Pro Ser Gln Ser Thr Gln Val Thr Thr Glu Glu Ala Pro
                85                  90                  95

Lys Thr Val Gln Ala Pro Lys Val Glu Thr Ser Arg Val Asp Leu Pro
            100                 105                 110

Ser Glu Lys Val Ala Asp Lys Glu Thr Thr Gly Thr Gln Val Asp Ile
        115                 120                 125

Ala Gln Pro Ser Asn Val Ser Glu Ile Lys Pro Arg Met Lys Arg Ser
    130                 135                 140

Thr Asp Val Thr Ala Val Ala Glu Lys Glu Val Val Glu Glu Thr Lys
145                 150                 155                 160

Ala Thr Gly Thr Asp Val Thr Asn Lys Val Glu Val Glu Glu Gly Ser
                165                 170                 175

Glu Ile Val Gly His Lys Gln Asp Thr Asn Val Val Asn Pro His Asn
            180                 185                 190

Ala Glu Arg Val Thr Leu Lys Tyr Lys Trp Lys Phe Gly Glu Gly Ile
        195                 200                 205

Lys Ala Gly Asp Tyr Phe Asp Phe Thr Leu Ser Asp Asn Val Glu Thr
    210                 215                 220

His Gly Ile Ser Thr Leu Arg Lys Val Pro Glu Ile Lys Ser Thr Asp
225                 230                 235                 240

Gly Gln Val Met Ala Thr Gly Glu Ile Ile Gly Glu Arg Lys Val Arg
                245                 250                 255

Tyr Thr Phe Lys Glu Tyr Val Gln Glu Lys Lys Asp Leu Thr Ala Glu
            260                 265                 270

Leu Ser Leu Asn Leu Phe Ile Asp Pro Thr Thr Val Thr Gln Lys Gly
        275                 280                 285
```

-continued

```
Asn Gln Asn Val Glu Val Lys Leu Gly Glu Thr Thr Val Ser Lys Ile
    290                 295                 300

Phe Asn Ile Gln Tyr Leu Gly Gly Val Arg Asp Asn Trp Gly Val Thr
305                 310                 315                 320

Ala Asn Gly Arg Ile Asp Thr Leu Asn Lys Val Asp Gly Lys Phe Ser
                325                 330                 335

His Phe Ala Tyr Met Lys Pro Asn Asn Gln Ser Leu Ser Ser Val Thr
            340                 345                 350

Val Thr Gly Gln Val Thr Lys Gly Asn Lys Pro Gly Val Asn Asn Pro
        355                 360                 365

Thr Val Lys Val Tyr Lys His Ile Gly Ser Asp Asp Leu Ala Glu Ser
    370                 375                 380

Val Tyr Ala Lys Leu Asp Asp Val Ser Lys Phe Glu Asp Val Thr Asp
385                 390                 395                 400

Asn Met Ser Leu Asp Phe Asp Thr Asn Gly Gly Tyr Ser Leu Asn Phe
                405                 410                 415

Asn Asn Leu Asp Gln Ser Lys Asn Tyr Val Ile Lys Tyr Glu Gly Tyr
            420                 425                 430

Tyr Asp Ser Asn Ala Ser Asn Leu Glu Phe Gln Thr His Leu Phe Gly
        435                 440                 445

Tyr Tyr Asn Tyr Tyr Tyr Thr Ser Asn Leu Thr Trp Lys Asn Gly Val
    450                 455                 460

Ala Phe Tyr Ser Asn Asn Ala Gln Gly Asp Gly Lys Asp Lys Leu Lys
465                 470                 475                 480

Glu Pro Ile Ile Glu His Ser Thr Pro Ile Glu Leu Glu Phe Lys Ser
                485                 490                 495

Glu Pro Pro Val Glu Lys His Glu Leu Thr Gly Thr Ile Glu Glu Ser
            500                 505                 510

Asn Asp Ser Lys Pro Ile Asp Phe Glu Tyr His Thr Ala Val Glu Gly
        515                 520                 525

Ala Glu Gly His Ala Glu Gly Thr Ile Glu Thr Glu Glu Asp Ser Ile
    530                 535                 540

His Val Asp Phe Glu Glu Ser Thr His Glu Asn Ser Lys His His Ala
545                 550                 555                 560

Asp Val Val Glu Tyr Glu Glu Asp Thr Asn Pro Gly Gly Gly Gln Val
                565                 570                 575

Thr Thr Glu Ser Asn Leu Val Glu Phe Asp Glu Asp Ser Thr Lys Gly
            580                 585                 590

Ile Val Thr Gly Ala Val Ser Asp His Thr Thr Ile Glu Asp Thr Lys
        595                 600                 605

Glu Tyr Thr Thr Glu Ser Asn Leu Ile Glu Leu Val Asp Glu Leu Pro
    610                 615                 620

Glu Glu His Gly Gln Ala Gln Gly Pro Ile Glu Glu Ile Thr Glu Asn
625                 630                 635                 640

Asn His His Ile Ser His Ser Gly Leu Gly Thr Glu Asn Gly His Gly
                645                 650                 655

Asn Tyr Gly Val Ile Glu Glu Ile Glu Glu Asn Ser His Val Asp Ile
            660                 665                 670

Lys Ser Glu Leu Gly Tyr Glu Gly Gly Gln Asn Ser Gly Asn Gln Ser
        675                 680                 685

Phe Glu Glu Asp Thr Glu Glu Asp Lys Pro Lys Tyr Glu Gln Gly Gly
    690                 695                 700

Asn Ile Val Asp Ile Asp Phe Asp Ser Val Pro Gln Ile His Gly Gln
```

-continued

```
705                 710                 715                 720

Asn Asn Gly Asn Gln Ser Phe Glu Glu Asp Thr Glu Lys Asp Lys Pro
                725                 730                 735

Lys Tyr Glu Gln Gly Gly Asn Ile Ile Asp Ile Asp Phe Asp Ser Val
            740                 745                 750

Pro His Ile His Gly Phe Asn Lys His Thr Glu Ile Ile Glu Glu Asp
        755                 760                 765

Thr Asn Lys Asp Lys Pro Asn Tyr Gln Phe Gly Gly His Asn Ser Val
    770                 775                 780

Asp Phe Glu Glu Asp Thr Leu Pro Gln Val Ser Gly His Asn Glu Gly
785                 790                 795                 800

Gln Gln Thr Ile Glu Glu Asp Thr Thr Pro Pro Ile Val Pro Pro Thr
                805                 810                 815

Pro Pro Thr Pro Glu Val Pro Ser Glu Pro Glu Thr Pro Thr Pro Pro
            820                 825                 830

Thr Pro Glu Val Pro Ser Glu Pro Glu Thr Pro Thr Pro Pro Thr Pro
        835                 840                 845

Glu Val Pro Thr Glu Pro Gly Lys Pro Ile Pro Pro Ala Lys Glu Glu
    850                 855                 860

Pro Lys Lys Pro Ser Lys Pro Val Glu Gln Gly Lys Val Val Thr Pro
865                 870                 875                 880

Val Ile Glu Ile Asn Glu Lys Val Lys Ala Val Val Pro Thr Lys Lys
                885                 890                 895

Ala Gln Ser Lys Lys Ser Glu Leu Pro Glu Thr Gly Gly Glu Glu Ser
            900                 905                 910

Thr Asn Asn Gly Met Leu Phe Gly Gly Leu Phe Ser Ile Leu Gly Leu
        915                 920                 925

Ala Leu Leu Arg Arg Asn Lys Lys Asn His Lys Ala
    930                 935                 940
```